United States Patent
Cowley et al.

(10) Patent No.: US 7,304,064 B2
(45) Date of Patent: Dec. 4, 2007

(54) 1-[(INDOL-3-YL)CARBONYL]PIPERAZINE DERIVATIVES

(75) Inventors: Phillip Martin Cowley, Scotland (GB); Wilson Caulfield, Scotland (GB); Jason Tierney, Scotland (GB); James Cairns, Scotland (GB); Julia Adam-Worrall, Scotland (GB); Mark York, Scotland (GB)

(73) Assignee: N.V. Organon, Oss (NL)

( * ) Notice: Subject to any disclaimer, the term of this patent is extended or adjusted under 35 U.S.C. 154(b) by 146 days.

(21) Appl. No.: 10/518,279

(22) PCT Filed: Jun. 13, 2003

(86) PCT No.: PCT/EP03/50226

§ 371 (c)(1),
(2), (4) Date: Dec. 15, 2004

(87) PCT Pub. No.: WO04/000832

PCT Pub. Date: Dec. 31, 2003

(65) Prior Publication Data
US 2005/0250760 A1  Nov. 10, 2005

(30) Foreign Application Priority Data
Jun. 21, 2002  (EP) .................. 02077505

(51) Int. Cl.
A61K 31/496 (2006.01)
A61K 31/4985 (2006.01)
C07D 403/06 (2006.01)
C07D 471/04 (2006.01)

(52) U.S. Cl. ............... 514/249; 514/254.09; 544/349; 544/373

(58) Field of Classification Search ............... 544/373, 544/349
See application file for complete search history.

(56) References Cited

FOREIGN PATENT DOCUMENTS

| EP | 1243268 | 9/2002 |
|---|---|---|
| WO | WO 98 06715 | 2/1998 |
| WO | WO 01 43746 | 6/2001 |
| WO | WO 01/58869 A2 | 8/2001 |

OTHER PUBLICATIONS

Huffman, J.W. et al.: "Design, Synthesis and Pharmacology of Cannabimimetic Indoles" Bioorganic & Medicinal Chemistry Letters,(1994) V4 N4 pp. 563-566, XP000651749 Oxford, GB.
Eissenstat, M.A. et al.: "AMINOALKYLINDOLES: Structure-Activity Relationships of . . . " Journal of Medicinal Chemistry, American Chemical Society (1995), V38 N16 pp. 3094-3105.
Battaglia et al., "Indole amide derivatives: synthesis, structure-activity relationaships and molecular modelling studies of a new series of histamine $H_1$receptor antagonists", Eur. J. Med. Chem. 34 1999) 93-105.
Dinsmore et. al., "Recent Advances in the Synthesis of Diketopiperazines," Tetrahedron 58 (2002) 3297-3312.
Duflos et. al., "N-Pyridinyl-Indole-3-(alkyl)carboxamides and derivatives as potential systemic and topical inflammation inhibitors," Eur. J. Med. Chem. 36 (2001) 545-553.
Howlett et. al., "International Union of Pharmacology, XXVII. Classification of Cannabinoid Receptors Pharmacol.," Pharmacol Rev 54 (2002) 161-202.
Iversen et. al. "Cannabinoids: a real prospect for pain relief?" Current Opinion in Pharmacology 2 (2002) 50-55.
Jacobsen et. al. "Piperazine Imidazo[1,5-a]quinoxaline Ureas as High Affinity $GABA_A$ Ligands of Dual Functionality," J. Med. Chem. 42 (1999) 1123-1144.
Jung et. al., "Organic Chemistry of L-Tyrosine. 1. General Synthesis of Chiral Piperazines from Amino Acids," J. Org. Chem 50 (1985) 4909-4913.
Peterson et. al., "Decaronylation of 3-Indoleglyoxalyl Chloride," J. Org. Chem. 23 (1958) 303-304.
Stratowa et al., "Use of a Luciferase Reporter System for Characterizing G-Protein-Linked Receptors," Curr. Opin. Biotech.6 (1995) 574-581.
Swain et. al., "Novel $5-HT_3$ Antagonists. Indole Oxadiazoles," J. Med. Chem. 34 (1991) 140-151.
Török et al., "General Synthesis of Methyl- and Dimethyl-cyclobutanes from Simple 1.3-Diols by Phase Transfer Catalysis," J. Chem. Soc. Perkin Trans. 1 (1993) 801-804.

Primary Examiner—Emily Bernhardt
(74) Attorney, Agent, or Firm—Susan Hess

(57) ABSTRACT

The present invention relates to 1-[(indol-3-yl)carbonyl] piperazine derivative according to the general formula I

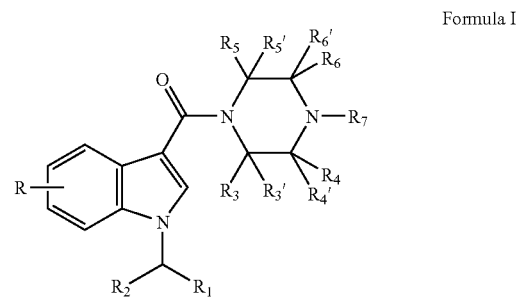

Formula I or a pharmaceutically acceptable salt thereof. The invention also relates to pharmaceutical compositions comprising said 1-[(indol-3-yl)carbonyl]piperazine derivatives, and to the use of these derivatives in the treatment of pain, such as peri-operative pain, chronic pain neuropathic pain, cancer pain, and pain and spasticity associated with multiple sclerosis.

8 Claims, No Drawings

1-[(INDOL-3-YL)CARBONYL]PIPERAZINE DERIVATIVES

This application is the 35 U.S.C. §371 filing of PCT/EP2003/050226 filed Jun. 13, 2003.

The present invention relates to 1-[(indol-3-yl)carbonyl]piperazine derivatives, to pharmaceutical compositions comprising the same and to the use of these 1-[(indol-3-yl)carbonyl]piperazine derivatives as cannabinoid agonists in the treatment of pain and other disorders.

1-[(Indol-3-yl)carbonyl]piperazine derivatives are known as compounds endowed with interesting pharmacological properties. 1-[(indol-3-yl)carbonyl]piperazine derivatives with unsubstituted indole nitrogen atom are disclosed in WO9806715 (SmithKlineBeecham Corp.) as anti-inflammatory agents. Related 1-[(indol-3-yl)carbonyl]piperazine derivatives which may also be substituted at the indole nitrogen atom are disclosed in WO0143746 (Nippon Shinyaku Co.) as compounds having antiinflammatory and nephrotropic activities.

1-[(1-Benzyl-indol-3-yl)carbonyl]piperazine derivatives were disclosed in a study on H1-receptor antagonists (Battaglia, S. et al. *Eur. J. Med. Chem.* 34, 93-105, 1999) and in a study on anti-inflammatory agents (Duflos, M. et al. *Eur. J. Med. Chem.* 36, 545-553, 2001), and found to be of relatively low activity in both studies. Recently 1-[(indol-3-yl)carbonyl]piperazine derivatives were generically described in WO0158869 (Bristol-Myers Squibb) as being active modulators of the cannabinoid receptor and as such useful in the treatment of respiratory diseases. No specific 1-[(indol-3-yl)carbonyl]piperazine derivatives were disclosed in this patent application.

Pain treatment is often limited by the side effects of currently available medication. For moderate to severe pain, opioids are widely used. These agents are cheap and effective but suffer from serious and potentially life-threatening side-effects, most notably respiratory depression and muscle rigidity. In addition, the doses of opioids which can be administered are limited by nausea, emesis, constipation, pruritis and urinary retention, often resulting in patients electing to receive sub-optimal pain control rather than suffer these distressing side effects. Furthermore, these side-effects often result in patients requiring extended hospitalisation. Opioids are highly addictive and are scheduled drugs in many territories. There is therefore a demand for new analgesics that have an improved side effect profile compared to currently used products, at equi-analgesic doses.

Evidence is accumulating that cannabinoid agonists have potential as analgesic and inflammatory agents. Two types of cannabinoid receptors are implicated, the cannabinoid CB1 receptor, which is located primarily in the central nervous system but which is also expressed by peripheral neurones and to a lower extent in other peripheral tissues, and the cannabinoid CB2 receptor, which is mostly located in immune cells (Howlett, A. C. et al.: International Union of Pharmacology. XXVII. Classification of Cannabinoid Receptors *Pharmacol. Rev.* 54, 161-202, 2002). While the CB2 receptor has been implicated in modulating the immune and antiinflammatory response of cannabinoids, cannabinoid receptor agonists, especially those acting at the CB1 receptor have recently been suggested as useful in the treatment of pain (Iversen, L. and Chapman, V.: *Cannabinoids: a real prospect for pain relief?* Current Opinion in Pharmacology, 2, 50-55, 2002 and references therein). Cannabinoid receptor agonists, such as CP 55,940 and WIN 55,212-2, produce potent antinociception with equivalent efficacy to morphine in animal models of acute pain, persistent inflammatory pain and neuropathic pain. The known cannabinoid agonists are in general highly lipophilic and insoluble in water. There is a thus a need for cannabinoid agonists with improved properties for use as therapeutic agents.

To this end the present invention provides 1-[(indol-3-yl)carbonyl]piperazine derivatives having the general formula I

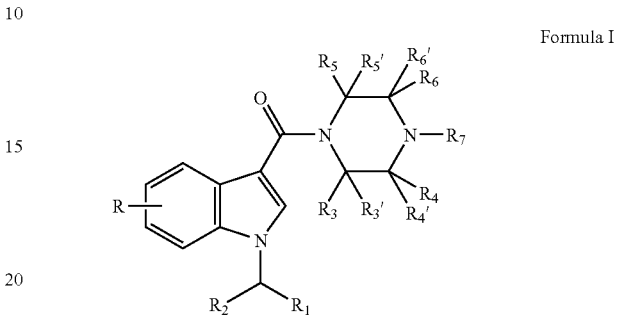

Formula I wherein
R represents 1-4 substituents independently selected from H, $(C_{1-4})$alkyl (optionally substituted with halogen), $(C_{1-4})$alkyloxy (optionally substituted with halogen), halogen, OH, $NH_2$, CN and $NO_2$;
$R_1$ is $(C_{5-8})$cycloalkyl or $(C_{5-8})$cycloalkenyl;
$R_2$ is H, methyl or ethyl;
$R_3$, $R_3'$, $R_4'R_4'$, $R_5$, $R_5'$ and $R_6'$ are independently hydrogen or $(C_{1-4})$alkyl, optionally substituted with $(C_{1-4})$alkyloxy, halogen or OH;
$R_6$ is hydrogen or $(C_{1-4})$alkyl, optionally substituted with $(C_{1-4})$alkyloxy, halogen or OH;
$R_6$ forms together with $R_7$ a 4-7 membered saturated heterocyclic ring, optionally containing a further heteroatom selected from O and S;
$R_7$ forms together with $R_6$ a 4-7 membered saturated heterocyclic ring, optionally containing a further heteroatom selected from O and S; or
$R_7$ is H, $(C_{1-4})$alkyl or $(C_{3-5})$cycloalkyl, the alkyl groups being optionally substituted with OH, halogen or $(C_{1-4})$alkyloxy; or
a pharmaceutically acceptable salt thereof, as agonists of the cannabinoid 1 receptor, which can therefore be used in the treatment of pain such as for example peri-operative pain, chronic pain, neuropathic pain, cancer pain and pain and spasticity associated with multiple sclerosis.

The compounds of the invention are generically described in WO0158869 (supra) as cannabinoid receptor modulators for treating respiratory disease. These modulators are preferentially identified therein as CB2 modulators. The majority of compounds which are disclosed in WO0158869 are characterized by the presence of a 2-(4-morpholinyl)ethyl side chain at the 1-position of an indole or indazole core structure. The 1-[(indol-3-yl)carbonyl]piperazine derivatives of the invention are distinguished from those of WO0158869 by having a cyclopentylmethyl- or a cyclohexylmethyl side chain at the corresponding position, a feature which, unlike a 2-(4-morpholinyl)ethyl side chain or a benzyl side chain, provides compounds having CB1 agonist activity.

The term $(C_{1-4})$alkyl as used in the definition of formula I means a branched or unbranched alkyl group having 1-4 carbon atoms, like butyl, isobutyl, tertiary butyl, propyl, isopropyl, ethyl and methyl.

In the term $(C_{1-4})$alkyloxy, $(C_{1-4})$alkyl has the meaning as defined above.

The term $(C_{5-8})$cycloalkyl means a saturated cyclic alkyl group having 5-8 carbon atoms, and can thus represent cyclopentyl, cyclohexyl, cycloheptyl or cyclooctyl.

Preferred $(C_{5-8})$cycloalkyl groups are cyclopentyl and cyclohexyl.

The term $(C_{5-8})$cycloalkenyl means a cyclic alkenyl group having 5-8 carbon atoms and at least one double bond, like cyclopent-3-enyl or cyclohex-3-enyl.

The term halogen means F, Cl, Br or I.

In the definition of formula I $R_6$ can form together with $R_7$ a 4-7 membered saturated heterocyclic ring, which means that $R_6$ together with the carbon atom to which it is bound and $R_7$ together with the nitrogen atom to which it is bound complete a 4-7 membered saturated ring, such as an azetidine, a pyrrolidine, a piperidine, or a 1H-azepine ring. Such rings may contain an additional O or S-heteroatom to form rings such as a morpholine, a piperazine, a homopiperazine, an imidazolidine or a tetrahydrothiazole ring.

There is a preference for 1-[(indol-3-yl)carbonyl]piperazine derivatives of formula I wherein $R_2$ is H and $R_1$ is a cyclopentyl or a cyclohexyl group.

More preferred are the compounds of formula I wherein in addition R represents $(C_{1-4})$alkyloxy or halogen, while even more preferred are the 1-[(indol-3-yl)carbonyl]-piperazine derivatives of the invention wherein R represents a methoxy group at the 7-position of the indole ring.

Especially preferred are the 1-[(indol-3-yl)carbonyl]piperazine derivatives of formula I wherein $R_3$, $R_3'$, $R_4'$, $R_5$, $R_5'$ and $R_6'$ are H; $R_4$, $R_6$ and $R_7$ are independently H or $(C_{1-4})$alkyl; or $R_6$ forms together with $R_7$ a 5- or 6-membered saturated heterocyclic ring and $R_4$ is H or $(C_{1-4})$alkyl.

Particular preferred CB-1 receptor agonists of the invention are:

1-{[1-(cyclohexylmethyl)-7-methoxy-1H-indol-3-yl]carbonyl}-3,5-dimethyl-4-ethylpiperazine;
1-{[1-(cyclohexylmethyl)-7-methoxy-1H-indol-3-yl]carbonyl}-3,4,5-trimethylpiperazine;
(S)-1-{[1-(cyclohexylmethyl)-7-methoxy-1H-indol-3-yl]carbonyl}-3,4-dinethyl-piperazine;
(S)-2-{[1-(cyclohexylmethyl)-7-methoxy-1H-indol-3-yl]carbonyl}-octahydro-2H-pyrido-2H-pyrido[1,2-a]pyrazine;
(S)-2-{[1-(cyclohexylmethyl)-7-methoxy-1H-indol-3-yl]carbonyl}-octahydro-2H-pyrrolo-[1,2-a]pyrazine; and
(S)-2-{[1-(cyclopentylmethyl)-7-methoxy-1H-indol-3-yl]carbonyl}-octahydro-2H-pyrido-[1,2-a]pyrazine; or pharmaceutically acceptable salts thereof.

The 1-[(indol-3-yl)carbonyl]piperazine derivatives of the invention may be prepared by methods known in the art of organic chemistry in general. More specifically such compounds can be prepared using procedures outlined by C. J. Swain et al (*J. Med. Chem.* 34, 140-151, 1991) and by P. E. Peterson, J. P. Wolf III and C. Niemann (*J. Org. Chem.* 23, 303-304, 1958) or by modification of these procedures.

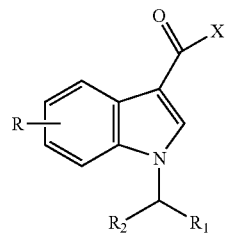

Formula II

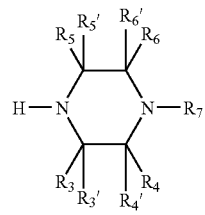

Formula III

1-[(Indol-3-yl)carbonyl]piperazines of Formula I can for instance be prepared from the condensation of a compound of Formula II, wherein $R_1$, $R_2$ and R have the meaning as previously defined and C(O)X represents a carboxylic acid or an activated derivative thereof, such as a carboxylic acid halide, preferably a chloride or a bromide, with a compound of Formula III where $R_3$-$R_7$ have the meaning as previously defined. When C(O)X represents a carboxylic acid (i.e., X is hydroxy) the condensation reaction can be effected with the aid of a coupling reagent, such as for example carbonyl diimidazole, dicyclohexylcarbodiimide and the like, in a solvent such as dimethylformamide or dichloromethane.

When C(O)X represents a carboxylic acid halide (i.e., X is halide) the condensation with the amine derivative III can be carried out in the presence of a base, for example triethylamine, in a solvent such as dichloromethane.

Compounds of formula III can be obtained from commercial sources, prepared by literature procedures or modifications of literature procedures known to those persons skilled in the art. For example, compounds of formula III can be prepared by reduction of a diketopiperazine, using a reducing agent such as lithium aluminium hydride or borane-tetrahydrofuran complex as described by M. E. Jung and J. C. Rohloff (*J. Org. Chem.* 50, 4909-4913, 1985). Diketopiperazines can be prepared by a variety of routes, as described by C. J. Dinsmore and D. C. Bershore (*Tetrahedron* 58, 3297-3312, 2002).

Compounds of formula II can be prepared by reaction of a compound of formula IV, where R has the meaning as previously defined, and a compound of formula V, where $R_1$ and $R_2$ have the meanings as previously defined and Y is a leaving group, for example a halide or an alkyl sulfonate, in the presence of a base such as sodium hydride. The carboxylic acid can be converted to a carboxylic acid halide, if desired, for example a carboxylic acid chloride, using a reagent such as oxalyl chloride.

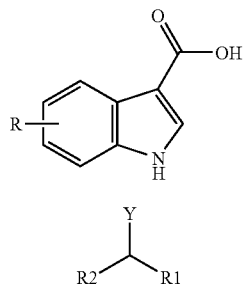

Formula IV

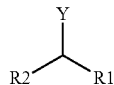

Formula V

Compounds of formula V can be obtained from commercial sources, prepared by literature procedures or modifications of literature procedures known to those persons skilled in the art.

For example, compounds of formula V where Y is para-toluenesulfonate can be prepared from compounds of formula V where Y is hydroxyl, using a method described by B. Török et al (*J. Chem. Soc. Perkin Trans.* 1, 801-804, 1993). Compounds of formula V where Y is hydroxyl and $R_2$ is hydrogen can be prepared by reduction of a carboxylic acid or carboxylic ester, using a reducing agent such as borane-tetrahydrofuran complex or lithium aluminium hydride.

Compounds of formula IV can be accessed from compounds of formula VI by acylation at the 3-position, using an acylating reagent. For example, compounds of formula IV can be accessed from compounds of formula VI by treatment with trifluoroacetic anyhydride in a solvent such as dimethylformamide, followed by hydrolysis in aqueous sodium hydroxide at an elevated temperature.

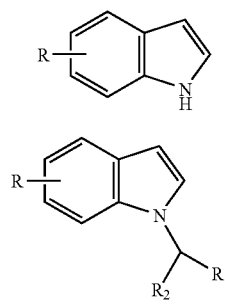

Formula VI

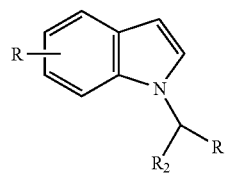

Formula VII

Compounds of formula VI can be obtained from commercial sources, prepared by literature procedures or modifications of literature procedures known to those persons skilled in the art.

Compounds of formula II can alternatively be prepared by acylation of a compound of formula VII, using an acylating reagent. For example, compounds of formula II where X is chloride can be prepared by reaction of a compound of formula VII with oxalyl chloride in a solvent such as 1,1,2,2-tetrachloroethane followed by rearrangement at elevated temperature.

Compounds of formula VII can be prepared by reaction of a compound of formula VI with a compound of formula V in the presence of a base such a sodium hydride.

The skilled person will likewise appreciate that various 1-[(indol-3-yl)carbonyl]-piperazine derivatives of Formula I can be obtained by appropriate conversion reactions of functional groups corresponding to certain of the substituents R and $R_1$-$R_7$. For example, compounds of formula I wherein $R_7$ is $(C_{1-4})$alkyl or $(C_{3-5})$cycloalkyl, the alkyl groups of which may be substituted with OH, halogen or $(C_{1-4})$alkyloxy, can be prepared by the reaction of a compound of formula I wherein $R_7$ is hydrogen with a $(C_{1-4})$ alkyl halide or a functionalised $(C_{1-4})$alkyl halide, in the presence of a base such as potassium carbonate.

Compounds of formula I wherein R is $(C_{1-4})$alkyloxy or functionalised $(C_{1-4})$alkyloxy may be prepared by the reaction of a compound of formula I wherein R is hydroxy with a $(C_{1-4})$alkyl halide or a functionalised $(C_{1-4})$alkyl halide, in the presence of a base such as sodium hydride.

Compounds of formula I wherein R is $NH_2$ may be prepared by the reaction of a compound of formula I wherein R is nitro with a reducing agent such as hydrogen/palladium on activated carbon.

The 1-[(indol-3-yl)carbonyl]piperazine derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

Pharmaceutically acceptable salts may be obtained by treating a free base of a compound of formula I with a mineral acid such as hydrochloric acid, hydrobromic acid phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid, methane sulfonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a 1-[(indol-3-yl)carbonyl]piperazine derivative having the general formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The 1-[(indol-3-yl)carbonyl]piperazine derivatives of the invention were found to be agonists of the CB-1 receptor, as determined in a human CB-1 reporter assay using CHO cells. Methods to determine receptor binding as well as in vitro biological activity of cannabinoid receptor modulators are well known in the art. In general, expressed receptor is contacted with the compound to be tested and binding or stimulation or inhibition of a functional response is measured.

To measure a functional response isolated DNA encoding the CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB1 expressing cell lines are well known in the art (Sambrook et al., Molecular Cloning: a Laboratory Manual, Cold Spring Harbor Laboratory Press, Cold Spring Harbor, latest edition). Expression of the receptor is attained by expression of the DNA encoding the desired protein. Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed CB1 (or CB2) receptor may be used to measure binding of compound.

For measurement of binding radioactively or fluorescently labeled compounds may be used. The most widely used radiolabelled cannabinoid probe is [$^3$H]CP55940, which has approximately equal affinity for CB1 and CB2 binding sites.

Another assay involves screening for cannabinoid CB1 agonist compounds by determining the second messenger response, such as for example measurment of receptor mediated changes in cAMP or MAPkinase pathways. Thus, such a method involves expression of the CB1 receptor on the cell surface of a host cell and exposing the cell to the test compound. The second messenger response is than measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene the expression of which correlates with receptor activation. In general, reporter gene expression might be controlled by any response element reacting to changing levels of second messenger-Suitable reporter genes are e.g. LacZ, alkaline phosphatase, firefly luciferase and green fluorescent protein. The principles of such transactivation assays are well known in the art and are described e.g. in Stratowa, Ch, Himmler, A and Czernilofsky, A. P., *Curr. Opin. Biotechnol.* 6, 574 (1995). For selecting active agonist compounds on the CB1 receptor the $EC_{50}$ value must be $<10^{-5}$ M, preferably $<10^{-7}$ M.

The compounds may be used in the treatment of pain such as for example perioperative pain, chronic pain, neuropathic pain, cancer pain and pain and spasticity associated with multiple sclerosis.

Cannabinoid agonists of the invention would also potentially be useful in the treatment of other disorders including multiple sclerosis, spasticity, inflammation, glaucoma, nausea and emesis, loss of appetite, sleep disturbances, respiratory disorders, allergies, epilepsy, migraine, cardiovascular disorders, neurodegenerative disorders, anxiety, traumatic brain injury and stroke.

The compounds could also be used in conjunction with other analgesic drugs such as opioids and non-steroidal anti-inflammatory drugs (NSAIDs), including COX-2 selective inhibitors.

The compounds of the invention may be administered for humans in a sufficient amount and for a sufficient amount of time to alleviate the symptoms. Illustratively, daily dosage levels for humans can be in the range of 0.001-50 mq per kg body weight, preferably in a daily dosage of 0.01-20 mg per kg body weight.

The invention is illustrated by the following Examples.

EXAMPLE 1

1-{[1-(Cyclohexylmethyl)-7-methoxy-1H-indol-3-yl]carbonyl}-4-ethylpiperazine, maleic acid salt To a solution of 7-methoxyindole (3.5 g, 23.8 mmol) in dimethylformamide (35 ml) at 0° C. was added trifluoroacetic anhydride (4.4 ml, 31.5 mmol) over 5 minutes. The mixture was stirred at room temperature for 1 h, then poured into water (200 ml). The resulting 7-methoxy-3-[(trifluoromethyl)carbonyl]indole precipitate was filtered off, washing with water and used directly in the next step.

The damp solid was suspended in 4 M sodium hydroxide solution (140 ml) and heated to reflux with stirring for 1 h. The mixture was cooled and washed twice with diethyl ether. The aqueous phase was then acidified to pH 1 using 5 M hydrochloric acid and the resulting fine precipitate filtered off, washed with water and dried to afford 7-methoxyindole-3-carboxylic acid (3.6 g).

7-Methoxyindole-3-carboxylic acid (3.0 g, 16.6 mmol) was added portionwise to a stirred suspension of sodium hydride (60% dispersion in mineral oil, 1.56 g, 39 mmol) in dimethylformamide (75 ml). After 1 h, bromomethylcyclohexane (5.7 g, 32.3 mmol) was added. The mixture was heated to 60° C. with stirring for 1 h. The mixture was diluted with water (250 ml) and washed with ethyl acetate and then diethyl ether. The aqueous phase was acidified to pH 1 using 5 M hydrochloric acid and the precipitate filtered off. The crude product was recrystallised from ethyl acetate to afford 1-(cyclohexylmethyl)-7-methoxyindole-3-carboxylic acid (3.75 g) as a crystalline solid.

To a solution of 1-(cyclohexylmethyl)-7-methoxyindole-3-carboxylic acid (2.5 g, 8.8 mmol) in THF (30 ml) was added oxalyl chloride (4.5 g, 35.3 mmol), dropwise with stirring. The mixture was stirred at room temperature for 18 h. The volatile components were evaporated under reduced pressure to afford 1-(cyclohexylmethyl)-7-methoxyindole-3-carbonyl chloride (2.7 g) as a crystalline solid.

To 1-(cyclohexylmethyl)-7-methoxyindole-3-carbonyl chloride (1.9 g, 6.2 mmol) was added a solution of N-ethylpiperazine (1.35 g, 11.8 mmol) in dichloromethane (60 ml). The mixture was stirred until the acid chloride dissolved. Triethylamine (3 ml, 21.5 mmol was added and the solution stirred at room temperature for 18 h. The reaction mixture was washed with water (2×50 ml), dried with sodium sulfate and evaporated to afford an oil. This was purified by flash chromatography eluting with 0-10% (v/v) methanol in dichloromethane to afford the title compound (free base) as a gum.

The free base was dissolved in diethyl ether (50 ml) and filtered into a stirred solution of maleic acid (0.83 g, 7.15 mmol) in ether (24 ml) and methanol (4 ml). The resulting mixture was stirred for 30 minutes and the solid filtered off. The solid was re-crystallised from methanol/diethyl ether to afford title compound (1:1 maleic acid salt) as a crystalline solid (2.7 g, 5.4 mmol). $^1$H NMR (400 MHz, CD$_3$OD) $\delta_H$ 0.99-1.08 (2H, m), 1.12-1.25 (3H, m), 1.36 (3H, t, J 7.5), 1.56 (2H, d, J 12.5), 1.63-1.74 (3H, m), 1.77-1.89 (1H, m), 3.22 (2H, q, J 7.5), 3.30-3.35 (4H, m), 3.95 (3H, s), 3.90-4.05 (4H, m), 4.25 (2H, d, J 7.0), 6.25 (2H, s, maleate) 6.76 (1H, d, J 7.5), 7.10 (1H, t, J 7.5), 7.26 (1H, d, J 7.5), 7.53 (1H, s); EIMS: m/z=384.4 [M+H]$^+$.

EXAMPLE 2

1-{[1-(Cyclopentylmethyl)-7-methoxy-1H-indol-3-yl]carbonyl}-4-ethylpiperazine, hydrochloride salt Cyclopentanemethanol p-toluenesulfonate was prepared by the following method: To a solution of cyclopentanemethanol (2.0 g, 20.0 mmol) and pyridine (2.9 ml, 36.3 mmol) in dichloromethane (20 ml) was added p-toluenesulfonyl chloride (3.46 g, 18.1 mmol). The mixture was stirred at room temperature for 24 h under nitrogen. The resulting mixture was washed with 2M hydrochloric acid and the aqueous layer separated and extracted with dichloromethane. The combined organics were dried over sodium sulphate and concentrated under reduced pressure to yield cyclopentanemethanol p-toluenesulfonate as a colourless oil (4.3 g, 17.0 mmol).

The title compound was prepared following the method of Example 1, using cyclopentanemethanol p-toluenesulfonate instead of bromomethylcyclohexane. $^1$H NMR (400MHz, CD$_3$OD) $\delta_H$ 1.29-1.35 (2H, m), 1.38 (3H, t, J 7.5), 1.52-1.71 (6H, m), 2.39-2.49 (1H, m), 3.24 (2H, q, J 7.5), 3.05-3.35 (2H, br m), 3.35-3.70 (4H, br m), 3.95 (3H, s), 4.38 (2H, d, J 7.5), 4.40-4.65 (2H, br m), 6.79 (1H, d, J 7.5), 7.10 (1H, t, J 7.5), 7.27 (1H, d, J 7.5), 7.60 (1H, s); EIMS: m/z=370.2 [M+H]$^+$.

EXAMPLE 3

The procedure described under Examples 1 and 2 was further used to prepare the following compounds:

3A: 1-{[1-(cycloheptylmethyl)-7-methoxy-1H-indol-3-yl]carbonyl}-4-ethylpierazine, hydrochloride salt was prepared using cycloheptanemethanol p-toluenesulfonate. EIMS: m/z=398.2 [M+H]$^+$.

3B: 1-{[1-(Cyclooctylmethyl)-7-methoxy-1H-indol-3-yl]carbonyl}-4-ethylpiperazine, hydrochloride salt was prepared using cyclooctanemethanol p-toluenesulfonate. EIMS: m/z=412.4 [M+H]$^+$.

3C: 1-{[1-(Cyclohexylmethyl)-7-methoxy-1H-indol-3-yl]carbonyl}-4-(2-hydroxyethyl)piperazine, trifluoroacetic acid salt was prepared following the method of Example 1, using 1-(2-hydroxyethyl)piperazine instead of N-ethylpiperazine. EIMS: m/z=400.2 [M+H]$^+$.

3D: 1-{[1-(Cyclohexylmethyl)-7-methoxy-1H-indol-3-yl]carbonyl}-4-(2-methoxyethyl)piperazine, trifluoroacetic acid salt was prepared using 1-(2-methoxyethyl)piperazine. EIMS: m/z=414.2 [M+H]$^+$.

3E: 1-{[1-(Cyclohexylmethyl)-7-methyl-1H-indol-3-yl]carbonyl}-4-ethylpiperazine was obtained following the method of Example 1, using 7-methylindole instead of 7-methoxyindole. EIMS: m/z=368.0 [M+H]$^+$.

3F: 1-{[1-(Cyclohexylmethyl)-7-ethyl-1H-indol-3-yl]carbonyl}-4-ethylpiperazine was obtained from 7-ethylindole. EIMS: m/z=382.2 [M+H]$^+$.

EXAMPLE 4

1-{[1-(Cyclohexylmethyl)-5-fluoro-1H-indol-3-yl]carbonyl}-4-ethylpiperazine, hydrochloride salt To a solution of 5-fluoro indole (1.0 g, 7.4 mmol) in dimethyl formamide (20 ml) was added sodium hydride (60% dispersion in mineral oil; 327 mg, 8.14 mmol). The mixture was stirred at room temperature for 10 minutes before the addition of bromomethylcyclohexane (1.3 ml, 9.3 mmol). The resulting mixture was stirred at room temperature for 15 hours. A further addition of sodium hydride (170 mg, 4.23 mmol) then bromomethylcyclohexane (0.65 ml, 4.65 mmol) was made and the reaction stirred for a further 15 hours.

The reaction was quenched with 2-propanol (10 ml) and then concentrated. The resulting brown gum was partitioned between ethyl acetate (50 ml) and 5% sodium hydrogen carbonate solution (50 ml). The organic layer was washed with water (50 ml), dried over sodium sulfate and concentrated. The crude intermediate was then purified by flash chromatography using 95% dichloromethane, 5% methanol as eluent, to afford 1-(cyclohexylmethyl)-5-fluoroindole (1.26 g, 5.45 mmol).

To a solution of 1-(cyclohexylmethyl)-5-fluoroindole (208 mg, 0.9 mmol) in 1,1,2,2-tetrachloroethane (15 ml) at 0° C., was added oxalyl chloride (0.122 ml, 0.945 mmol) with stirring under a stream of nitrogen. The mixture was allowed to warm to room temperature over 1 hour, then heated to 120° C. for a further 1.5 hours. The mixture was cooled to room temperature and triethylamine (0.138 ml, 0.99 mmol) was added. Stirring was continued for a further 10 minutes before the addition of N-ethylpiperazine (0.125 ml, 0.99 mmol). The mixture was stirred at room temperature for 15 hours and then partitioned between 0.4 M sodium hydroxide solution (10 ml) and dichloromethane (10 ml). The organic layer was washed with water (10 ml), dried over $Na_2SO_4$ and concentrated. The resulting brown oil was purified by flash chromatography using 95% dichloromethane, 5% methanol as eluent to yield the title compound as the free base.

Hydrochloride salt formation was achieved by the addition of hydrogen chloride 2M solution in diethyl ether (3 ml) to a solution of the free base in diethyl ether (5 ml). The precipitate was filtered and dried. The solid was crystallised from diethyl ether and methanol to afford title compound (1:1 hydrochloric acid salt) as a crystalline solid (0.172 g, 0.42 mmol). $^1$H NMR (400 MHz, $CD_3OD$) $\delta_H$ 0.98-1.27 (2H, m), 1.17-1.27 (3H, m), 1.39 (3H, t, J 7.5), 1.59 (2H, d, J 13.0), 1.64-1.77 (3H, m), 1.83-1.93 (1H, m), 3.08-3.20 (2H, m), 3.24-3.33 (2H, m), 3.51 (2H, t, J 12.5), 3.63 (2H, d, J 11.0), 4.07 (2H, d, J 7.5), 4.58 (2H, d, J 13.5), 7.04 (1H, td, J 9.0, 2.5), 7.45 (1H, dd, J 9.5, 2.5), 7.47-7.51 (1H, m), 7.77 (1H, s).; EIMS: m/z=372.0 [M+H]$^+$.

EXAMPLE 5

The procedure described under Example 4 was further used to prepare the following compounds:

5A: 1-{[1-(Cyclohexylmethyl)-6-fluoro-1H-indol-3-yl]carbonyl}-4-ethylpiperazine, hydrochloride salt was obtained from 6-fluoroindole. EIMS: m/z=372.0 [M+H]$^+$.

5B: 1-{[1-(Cyclohexylmethyl)-7-fluoro-1H-indol-3-yl]carbonyl}-4-ethylpiperazine, hydrochloride salt was obtained from 7-fluoroindole. EIMS: m/z=372.0 [M+H]$^+$.

5C: 1-{[6-Bromo-1-(cyclohexylmethyl)-1H-indol-3-yl]carbonyl}-4-ethylpiperazine, hydrochloride salt was obtained from 6-bromoindole. EIMS: m/z=432.4 [M+H]$^+$.

5D: 1-{[7-Bromo-1-(cyclohexylmethyl)-1H-indol-3-yl]carbonyl}-4-ethylpiperazine, hydrochloride salt was obtained from 7-bromoindole. EIMS: m/z=432.5 [M+H]$^+$.

5E: 1-{[5-Chloro-1-(cyclohexylmethyl)-1H-indol-3-yl]carbonyl}-4-ethylpiperazine, hydrochloride salt was obtained from 5-chloroindole. EIMS: m/z=388.2 [M+H]$^+$.

5F: 1-{[6-Chloro-1-(cyclohexylmethyl)-1H-indol-3-yl]carbonyl}-4-ethylpiperazine, hydrochloride salt was obtained from 6-chloroindole. EIMS: m/z=388.5 [M+H]$^+$.

5G: 1-{[7-Chloro-1-(cyclohexylmethyl)-1H-indol-3-yl]carbonyl}-4-ethylpiperazine, hydrochloride salt was obtained from 7-chloroindole. EIMS: m/z=388.0 [M+H]$^+$.

5H: 1-{[6-Cyano-1-(cyclohexylmethyl)-1H-indol-3-yl]carbonyl}-4-ethylpiperazine, hydrochloride salt was obtained from 6-cyanoindole. EIMS: m/z=379.4 [M+H]$^+$.

5I: 1-{[1-(1-Cyclohexylethyl)-1H-indol-3-yl]carbonyl}-4-ethylpiperazine, hydrochloride salt was obtained from indole and racemic 1-cyclohexyl-1-p-toluenesulfonyl ethane. EIMS: m/z=368.0 [M+H]$^+$.

The product obtained in Example 5I was subjected to chiral HPLC separation on a Chiracel®OD column (2 cm×25 cm), eluting with isohexane/isopropanol 95/5 (v/v) at 20 ml/min flow rate. The products were detected using a UV detector at a wavelength of 240 nm.

(−)-5I: Enantiomer 1; retention time 8.1 minutes; enantiomeric excess >98%, $[\alpha]_D^{22}$−12° (c=1.25 mg/ml in $CHCl_3$).

(+)-5I: Enantiomer 2; retention time 11.1 minutes; enantiomeric excess >98%, $[\alpha]_D^{22}$+7° (c=1.50 mg/ml in $CHCl_3$).

5J: 1-{[1-(1-Cyclohexylethyl)-6-methoxy-1H-indol-3-yl]carbonyl}-4-ethylpiperazine, hydrochloride salt was obtained from 6-methoxyindole and 1-cyclohexyl-1-p-toluenesulfonyl ethane. EIMS: m/z=398.2 [M+H]$^+$.

5K: 1-{[1-(1-Cyclohexylethyl)-7-methoxy-1H-indol-3-yl]carbonyl}-4-ethylpiperazine, hydrochloride salt was obtained from 7-methoxyindole and 1-cyclohexyl-1-p-toluenesulfonyl ethane. EIMS: m/z=398.2 [M+H]$^+$.

5L: 1-{[1-(Cyclohexylmethyl)-6-nitro-1H-indol-3-yl]carbonyl}-4-ethylpiperazine, hydrochloride salt was obtained from 6-nitroindole. EIMS: m/z=399.2 [M+H]$^+$.

5M: 1-{[1-(Cyclohexylmethyl)-7-nitro-1H-indol-3-yl]carbonyl}-4-ethylpiperazine, hydrochloride salt was obtained from 7-nitroindole. EIMS: m/z=399.2 [M+H]$^+$.

5N: 1-{[7-Benzyloxy-1-(cyclohexylmethyl)-1H-indol-3-yl]carbonyl}-4-ethylpiperazine, hydrochloride salt was obtained from 7-benzyloxyindole. EIMS: m/z=460.4 [M+H]$^+$.

5O: 1-{[1-(Cyclohexylmethyl)-6-methoxy-1H-indol-3-yl]carbonyl}-4-ethylpiperazine, maleic acid salt was obtained from 6-methoxyindole. EIMS: m/z=384.5 [M+H]$^+$.

5P: 1-{[1-(Cyclohexylmethyl)-7-methoxy-1H-indol-3-yl]carbonyl}-4-isopropylpiperazine, hydrochloride salt was obtained from 7-methoxyindole and 1-isopropylpiperazine. EIMS: m/z=398.2 [M+H]$^+$.

5Q: 1-{[1-(Cyclohex-3-enylmethyl)-7-methoxy-1H-indol-3-yl]carbonyl}-4-ethylpiperazine was obtained from 7-methoxyindole and cyclohex-3-enemethanol p-toluenesulfonate. EIMS: m/z=382.2 [M+H]$^+$.

5R: 1-{[6-Bromo-1-(cyclohexylmethyl)-1H-indol-3-yl]carbonyl}-4-methylpiperazine, hydrochloride salt was obtained using 6-bromoindole as starting material and N-methyl piperazine instead of N-ethyl piperazine. EIMS: m/z=374 2 [M+H]$^+$.

5S: 1-{[1-(Cyclohexylmethyl)-5-fluoro-1H-indol-3-yl]carbonyl}-4-methylpiperazine, hydrochloride salt was obtained using 5-fluoroindole and N-methyl piperazine. EIMS: m/z=358.2 [M+H]$^+$.

5T: 1-{[1-(Cyclohexylmethyl)-6-fluoro-1H-indol-3-yl]carbonyl}-4-methylpiperazine, hydrochloride salt was obtained from 6-fluoroindole and N-methyl piperazine. EIMS: m/z=358.0 [M+H]$^+$.

5U: 1-{[1-(Cyclohexylmethyl)-7-fluoro-1H-indol-3-yl]carbonyl}-4-methylpiperazine, hydrochloride salt was obtained from 7-fluoroindole and N-methyl piperazine. EIMS: m/z=358.0 [M+H]$^+$.

5V: 1-{[6-Chloro-1-(cyclohexylmethyl)-1H-indol-3-yl]carbonyl}-4-methylpiperazine, hydrochloride salt was obtained from 6-chloroindole and N-methyl piperazine. EIMS: m/z=374.0 [M+H]$^+$.

5W: 1-{[7-Chloro-1-(cyclohexylmethyl)-1H-indol-3-yl]carbonyl}-4-methylpiperazine, hydrochloride salt was obtained from 7-chloroindole and N-methyl piperazine. EIMS: m/z=374.2 [M+H]$^+$.

5X: 1-{[6-Cyano-1-(cyclohexylmethyl)1H-indol-3-yl]carbonyl}-4-methylpiperazine, hydrochloride salt was obtained from 6-cyanoindole and N-methylpiperazine. EIMS: m/z=365.0 [M+H]$^+$.

5Y: 1-{[1-(1-Cyclohexylethyl)-6-methoxy-1H-indol-3-yl]carbonyl}-4-methylpiperazine, hydrochloride salt was obtained from 6-methoxyindole, N-methylpiperazine and 1-cyclohexyl-1-p-toluenesulfonyl ethane. EIMS: m/z=384.2 [M+H]$^+$.

5Z: 1-{[1-(1-Cyclohexylpropyl)-1H-indol-3-yl]carbonyl}-4-methylpiperazine, hydrochloride salt was obtained from indole, N-methylpiperazine and 1-cyclohexyl-1-p-toluenesulfonyl propane. EIMS: m/z=368.0 [M+H]$^+$.

EXAMPLE 6

1-{[7-Amino-1-(cyclohexylmethyl)-1H-indol-3-yl]carbonyl}-4-ethylpiperazine

4-{[1-(Cyclohexylmethyl)-7-nitro-1H-indol-3-yl]carbonyl}-1-ethylpiperazine (200 mg, 0.5 mmol) was dissolved in methanol (10 ml) to which was added palladium (5 wt. % on activated carbon; 50 mg, cat.) as a slurry in methanol (3 ml). The system was then sealed and flushed with nitrogen before fixing a hydrogen source (balloon). The mixture was stirred at room temperature under hydrogen for 15 hours after which it was filtered through celite and concentrated. The resulting brown oil was purified by flash chromatography using 95% dichloromethane, 5% methanol as eluent to yield the title product as the free base. $^1$H NMR (400 MHz, CD$_3$OD) $\delta_H$ 0.97-1.08 (2H, m), 1.12 (3H, t, J 7.5), 1.17-1.26 (3H, m), 1.53 (2H, d, J 12.5), 1.63-1.75)(3H m) 1.87-1.98 (1H, m), 2.44-2.55 (6H, m), 3.37 (4H, t, J 5.0), 4.20 (2H, d, J 7.5), 6.59 (1H, dd, J 7.5, 1.0), 6.93 (1H, t, J 7.5), 7.06 (1H, dd, J 8.0, 1.0), 7.39 (1H, s); EIMS: m/z=369.0 [M+H]$^+$.

EXAMPLE 7

1-{[1-(Cyclohexylmethyl)-7-hydroxy-1H-indol-3-yl]carbonyl}-4-ethylpiperazine, hydrochloride salt To a solution of 4-{[7-benzyloxy-1-(cyclohexylmethyl)-1H-indole-3-yl]carbonyl}-1-ethylpiperazine (1 g, 2.2 mmol) in ethanol (50 ml), was added palladium (5 wt. % on activated carbon; 100 mg). The mixture was hydrogenated under a pressure of 5.5 bar at 60° C. for 16 hours. The resulting mixture was filtered through dicalite, and the filtrate concentrated under reduced pressure to afford the title compound (free base) as a gum (865 mg, 2.3 mmol).

Hydrochloride salt formation was achieved by the addition of hydrogen chloride (2M solution in diethyl ether, 3 ml) to a solution of the free base (180 mg, 0.5 mmol) in diethyl ether (5 ml). The precipitate was filtered and dried. The solid was crystallised from diethyl ether and ethanol to afford the title compound (1:1 hydrochloric acid salt) as a crystalline solid (132 mg, 0.3 mmol). $^1$H NMR (400 MHz, CD$_3$OD) $\delta_H$ 1.05 (2H, m), 1.19 (3H, m), 1.38 (3H, t, J 7.5), 1.57 (2H, m), 1.69 (3H, m), 1.92 (1H, m), 3.13 (2H, m), 3.27 (2H, q, J 7.5), 3.45 (2H, m), 3.61 (2H, d, J 12.0), 4.29 (2H, d, J 7.0), 4.55 (2H, d, J 14.0), 6.59 (1H, d, J 7.0), 6.97 (1H, t, J 7.0), 7.14 (1H, d, J 7.0), 7.52 (1H, s); EIMS: m/z=370.2 [M+H]$^+$.

EXAMPLE 8

1-{[1-(Cyclohexylmethyl)-7-(2-fluoroethoxy)-1H-indol-3-yl]carbonyl}-4-ethylpiperazine Sodium hydride (60% dispersion in mineral oil, 65 mg, 1.62 mmol) was added portionwise with stirring under a stream of nitrogen to a solution of 4-{[1-(cyclohexylmethyl)-7-hydroxy-1H-indole-3-yl]carbonyl}-1-ethylpiperazine (200 mg, 0.54 mmol) in dimethylformamide (5 ml). After 30 minutes, 1-bromo-2-fluoroethane (49 µl, 0.65 mmol) was added. The mixture was heated to 60° C. with stirring for 48 hours. The reaction was quenched with 2-propanol (10 ml) and then concentrated. The resulting brown gum was partitioned between dichloromethane (50 ml) and 5% sodium hydrogen carbonate solution (50 ml). The organic layer was washed with water (50 ml), dried over sodium sulfate and concentrated. The crude intermediate was purified by flash chromatography using 95% dichloromethane, 5% methanol as eluent to afford the title compound (54 mg, 0.1 mmol). $^1$H NMR (400 MHz, CD$_3$OD) $\delta_H$ 1.05 (2H, m), 1.19 (3H, m), 1.39 (3H, t, J 7.5), 1.56 (2H, m), 1.69 (3H, m), 1.92 (1H, m), 2.48 (2H, q, J 7.0), 2.53 (4H, m), 3.75 (4H, t, J 5.0), 4.26 (2H, d, J 7.5), 4.32 (1H, m), 4.39 (1H, m), 4.75 (1H, m), 4.87 (1H, m), 6.73 (1H, d, J 8.0), 7.06 (1H, t, J 8.0), 7.26 (1H, d, J 8.0), 7.44 (1H, s); EIMS: m/z=416.2 [M+H]$^+$.

EXAMPLE 9

1-{[1-(Cyclohexylmethyl)-7-ethoxy-1H-indol-3-yl]carbonyl}-4-ethylpiperazine was prepared following the procedure described under example 8, using bromoethane instead of 1-bromo-2-fluoroethane. EIMS: m/z=398.2 [M+H]$^+$.

EXAMPLE 10

1-{[1-(Cyclohexylmethyl)-7-methoxy-1H-indol-3-yl]carbonyl}-2,3,5,6-tetramethylpiperazine, hydrochloride salt To a solution of diisopropylethylamine (0.83 ml, 4.90 mmol) and 2,3,5,6-tetramethylpiperazine (0.35 g, 2.45 mmol) in dichloromethane (5 ml) was added a solution of 1-(cyclohexylmethyl)-7-methoxyindole-3-carbonyl chloride (0.33 g, 1.08 mmol, prepared following the method in Example 1) in dichloromethane (5 ml). The mixture was stirred at room temperature for 6 h, evaporated under reduced pressure and the residue purified by flash chromatography eluting with 5-10% (v/v) methanol in dichloromethane to afford the title compound (free base) as a colourless oil (0.43 g). The free base (0.1 g, 0.24 mmol) was dissolved in dichloromethane (1 ml), treated dropwise with 2 M hydrochloric acid in diethyl ether (0.3 ml) and diethyl ether (3 ml). The resulting precipitate was collected by filtration, washed with diethyl ether (15 ml) and dried under reduced pressure to afford the title compound (1:1 hydrochloric acid salt) as a white solid (0.09 g, 0.20 mmol). $^1$H NMR (400 MHz, CD$_3$OD) $\delta_H$ 0.98-1.39 (8H, m), 1.42 (6H, d, J 7.0), 1.64-1.89 (9H, m), 3.44-3.70 (3H, m), 3.95 (3H, s), 4.21-4.34 (3H, m), 6.77 (1H, d, J 7.7), 7.11 (1H, t, J 8.2), 7.38 (1H, d, J 8.2), 7.58 (1H, s); EIMS: m/z 412.4 [M+H]$^+$.

EXAMPLE 11

1-{[1-(Cyclohexylmethyl)-7-methoxy-1H-indol-3-yl]carbonyl}-2,6-dimethylpiperazine, hydrochloride salt 4-{[1-(Cyclohexylmethyl)-7-methoxy-1H-indol-3-yl]carbonyl}-3,5-dimethylpiperazine-1-carboxylic acid tert-butyl ester was prepared following the method in Example 10 using 3,5-dimethylpiperazine-1-carboxylic acid tert-butyl ester (E. J. Jacobsen et al; *J. Med. Chem.* 42, 1123-1144, 1999) instead of 2,3,5,6-tetramethylpiperazine. To an ice cooled solution of 4-{[1-(cyclohexylmethyl)-7-methoxy-1H-indol-3-yl]carbonyl}-3,5-dimethylpiperazine-1-carboxylic acid tert-butyl ester (0.52 g, 1.08 mmol) in dichloromethane (5 ml) was added dropwise trifluoroacetic acid (2 ml). The mixture was allowed to warm to room temperature over 2 h before removal of any volatile components under reduced pressure. The residue was then suspended in 5 M sodium hydroxide solution (10 ml) and extracted into dichloromethane (2×30 ml). The combined organic layers were dried with magnesium sulfate and evaporated to an oil. This was purified by flash chromatography eluting with 5-10% (v/v) methanol in dichloromethane to afford the title compound (free base) as a colourless oil. The free base was dissolved in diethyl ether (3 ml) and treated dropwise with 2 M hydrochloric acid in diethyl ether (1 ml). The resulting precipitate was collected by filtration, washed with diethyl ether (15 ml) and dried under reduced pressure to afford the title compound (1:1 hydrochloric acid salt) as a colourless solid (0.13 g, 0.31 mmol). $^1$H NMR (400 MHz, CD$_3$OD) δ$_H$ 1.04 (2H, brq, J 9.0), 1.11-1.25 (3H, m), 1.44 (6H, d, J 7.0), 1.54 (2H, br d, J 13.0), 1.62-1.90 (4H, m), 3.33-3.42 (4H, m), 3.95 (3H, s), 4.26 (2H, d, J 7.0), 4.74-4.86 (2H, m), 6.76 (1H, d, J 7.5), 7.09 (1H, t, J 8.0), 7.21 (1H, d, J 7.5), 7.46 (1H, s); EIMS: m/z 384.2 [M+H]$^+$.

EXAMPLE 12

1-{[1-(Cyclohexylmethyl)-7-methoxy-1H-indol-3-yl]carbonyl}-3,5-dimethylpiperazine, hydrochloride salt To a solution of 1-(cyclohexylmethyl)-7-methoxy-indole-3-carboxylic acid (0.25 g, 0.87 mmol, prepared following the method in Example 1) and 2,6-dimethylpiperazine (0.12 g, 1.05 mmol) in dichloromethane (10 ml) was added diisopropylcarbodiimide (0.16 ml, 1.05 mmol) and 1-hydroxybenzotriazole (0.01 g, 0.09 mmol). The mixtures was stirred at room temperature for 18 h. The mixture was washed with 5 M sodium hydroxide (2×10 ml), dried with magnesium sulfate and evaporated. The residue was purified by flash chromatography eluting with 5-10% (v/v) methanol in dichloromethane to afford the title compound (free base) as a colourless oil. The free base (0.15 g) was dissolved in diethyl ether (3 ml) and treated dropwise with 2 M hydrochloric acid in diethyl ether (1 ml). The resulting precipitate was collected by filtration, washed with diethyl ether (15 ml) and dried under reduced pressure to afford the title compound (1:1 hydrochloric acid salt) as a colourless solid (0.15 g, 0.36 mmol). $^1$H NMR (400 MHz, CD$_3$OD) δ$_H$ 0.98-1.26 (5H, m) 1.32 (6H, d, J 6.5), 1.56 (2H, brd, J 12.0), 1.62-1.90 (4H, m), 3.06 (2H, dd, J 14.5, 11.5), 3.39-3.50 (2H, m), 3.95 (3H, s), 4.26 (2H, d, J 7.5), 4.52 (2H, br d, J 13.5), 6.77 (1H, d, J 7.5), 7.1 (1H, t, J 8.0), 7.24 (1H, d, J 8.0), 7.54 (1H, s); EIMS: m/z 384.2 [M+H]$^+$.

EXAMPLE 13

The procedure described under example 12 was further used to prepare the following compounds:

13A: 1-{[1-(Cyclohexylmethyl)-7-methoxy-1H-indol-3-yl]carbonyl}-3-methylpiperazine, hydrochloride salt was prepared using 1-(cyclohexylmethyl)-7-methoxy-indole-3-carboxylic acid and rac-2-methylpiperazine. $^1$H NMR (400 MHz, CD$_3$OD) δ$_H$ 0.98-1.24 (6H, m), 1.33 (3H, d, J 6.5), 1.56 (2H, br d, J 12.5), 1.63-1.88 (4H, m), 3.17-3.22 (2H, m), 3.39-3.51 (3H, m), 3.94 (3H, s), 4.26 (2H, d, J 7.0), 4.43 (2H, br d, J 14.0), 6.76 (1H, d, J 7.5), 7.1 (1H, t, J 7.5), 7.25 (1H, d, J 8.0), 7.54 (1H, s). EIMS; m/z=370.2 [M+H]$^+$.

13B: 1-{[1-(Cyclopentylmethyl)-7-methoxy-1H-indol-3-yl]carbonyl}-3,5-dimethylpiperazine, hydrochloride salt was prepared using 1-(cyclopentylmethyl)-7-methoxy-indole-3-carboxylic acid and 2,6-dimethylpiperazine. $^1$H NMR (400 MHz, CD$_3$OD) δ$_H$ 1.24-1.36 (8H, m), 1.51-1.72 (6H, m), 2.43 (1H, heptet, J 7.5), 3.07 (2H, dd, J 14.5, 11.5), 3.39-3.50 (2H, m), 3.95 (3H, s), 4.37 (2H, d, J 7.5), 4.52 (2H, d, J 14.0), 6.77 (1H, d, J 7.5), 7.10 (1H, t, J 7.5), 7.24 (1H, d, J 8.0), 7.59 (1H, s). EIMS; m/z=370.2 [M+H]$^+$.

13C: (S)-1-{[1-(Cyclopentylmethyl)-7-methoxy-1H-indol-3-yl]carbonyl}-3-methylpiperazine, hydrochloride salt was prepared using 1-(cyclopentylmethyl)-7-methoxy-indole-3-carboxylic acid and (S)-2-methylpiperazine. $^1$H NMR (400 MHz, CD$_3$OD) δ$_H$ 1.26-1.36 (5H, m), 1.51-1.72 (6H, m), 2.42 (1H, heptet, J 7.7), 3.20 (2H, dd, J 14.5, 10.9), 3.38-3.5 (3H, m), 3.95 (3H, s), 4.37 (2H, d, J 7.5), 4.43 (2H, br d, J 14.5), 6.77 (1H, d, J 7.6), 7.10 (1H, t, J 7.7), 7.25 (1H, d, J 8.1), 7.59 (1H, s). EIMS; m/z=356.2 [M+H]$^+$.

13D: 1-{[1-(Cyclohexylmethyl)-7-methoxy-1H-indol-3-yl]carbonyl}-3,3-dimethylpiperazine, hydrochloride salt was prepared using 1-(cyclohexylmethyl)-7-methoxy-indole-3-carboxylic acid and 2,2-dimethylpiperazine. $^1$H NMR (400 MHz, CD$_3$OD) δ$_H$ 1.10-1.22 (5H, m), 1.38 (6H, s), 1.54-1.86 (6H, m), 3.31-3.34 (2H, m), 3.2 (2H, dd, J 14.5, 10.9), 3.81 (2H, s), 3.95 (3H, s), 3.96-3.99 (2H, m), 4.26 (2H, d, J 7.1), 6.76 (1H, d, J 7.5), 7.10 (1H, t, J 8.1), 7.24 (1H, d, J 8.0), 7.53 (1H, s). EIMS; m/z=384.5 [M+H]$^+$.

13E: (S)-1-{[1-(Cyclohexylmethyl)-7-methoxy-1H-indol-3-yl]carbonyl}-3-methylpiperazine, hydrochloride salt was prepared using 1-(cyclohexylmethyl)-7-methoxy-indole-3-carboxylic acid and (S)-2-methylpiperazine. $^1$H NMR (400 MHz, CD$_3$OD) δ$_H$ 1.01-1.23 (5H, m), 1.33 (3H, d, J 6.5), 1.52-1.87 (6H, m) 3.16-3.27 (2H, m), 3.38-3.51 (3H, m), 3.95 (3H, s), 4.27 (2H, d, J 7.0), 4.43 (2H, br d, J 14.3), 6.76 (1H, d, J 7.8), 7.10 (1H, t, J 7.9), 7.25 (1H, d, J 8.0), 7.54 (1H, s). EIMS; m/z=370.0 [M+H]$^+$.

13F: (R)-1-{[1-(Cyclohexylmethyl)-7-methoxy-1H-indol-3-yl]carbonyl}-3-methylpiperazine, hydrochloride salt was prepared using 1-(cyclohexylmethyl)-7-methoxy-indole-3-carboxylic acid and (R)-2-methylpiperazine. $^1$H NMR (400 MHz, CD$_3$OD) δ$_H$ 1.01-1.23 (5H, m), 1.33 (3H, d, J 6.5), 1.52-1.87 (6H, m), 3.16-3.27 (2H, m), 3.38-3.51 (3H, m), 3.95 (3H, s), 4.27 (2H, d, J 7.0), 4.43 (2H, br d, J 14.3), 6.76 (1H, d, J 7.8), 7.10 (1H, t, J 7.9), 7.25 (1H, d, J 8.0), 7.54 (1H, s). EIMS; m/z=370.0 [M+H]$^+$.

EXAMPLE 14

1-{[1-(Cyclohexylmethyl)-7-methoxy-1H-indol-3-yl]carbonyl}-3,5-dimethyl-4-ethylpiperazine, hydrochloride salt To a solution of 1-{[1-(Cyclohexylmethyl)-1H-indol-3-yl]carbonyl}-3,5-dimethylpiperazine (0.7 g, 1.83 mmol) and potassium carbonate (0.3 g, 2.19 mmol) in dimethylformamide (5 ml) was added iodoethane (0.17 ml, 2.10 mmol). The mixture was heated to 50° C. for 18 h and diluted with water (20 ml). The suspension was then extracted with methyl tert-butyl ether (2×30 ml), the combined organic layers washed with water (3×20 ml), dried with magnesium sulfate and evaporated. The residue was purified by flash chromatography eluting with 5-10% (v/v) methanol in dichloromethane to afford the title compound (free base) as a colourless oil. The free base (0.42 g) was dissolved in diethyl ether (10 ml) and treated dropwise with 2 M hydrochloric acid in diethyl ether (1 ml). The resulting precipitate was collected by filtration, washed with diethyl ether (15 ml) and dried under reduced pressure to afford the title compound (1:1 hydrochloric acid salt) as a white solid (0.35 g, 0.78 mmol). $^1$H NMR (400 MHz, CD$_3$OD) $\delta_H$ 0.98-1.23 (5H, m), 1.30 (3H, t, J 7.0), 1.39 (6H, d, J 7.0), 1.53-1.88 (6H, m), 3.22-3.35 (2H, m), 3.42-3.61 (4H, m), 3.95 (3H, s), 4.26 (2H, d, J 7.0), 4.53 (2H, br d, J 13.0), 6.77 (1H, d, J 8.0), 7.10 (1H, t, J 8.0), 7.27 (1H, d, J 8.0), 7.57 (1H, s). EIMS: m/z 412.4 [M+H]$^+$.

EXAMPLE 15

The procedure described under example 14 was further used to prepare the following compounds:

15A: 1-{[1-(Cyclopentylmethyl)-7-methoxy-1H-indol-3-yl]carbonyl}-3,5-dimethyl-4-ethylpiperazine, hydrochloride salt was prepared using 1-{[1-(cyclopentylmethyl)-7-methoxy-1H-indol-3-yl]carbonyl}-3,5-dimethylpiperazine. $^1$H NMR (400 MHz, CD$_3$OD) $\delta_H$ 1.27-1.40 (5H, m), 1.39 (6H, d, J 6.5) 1.73-1.43 (6H, m), 2.44 (1H heptet J 7.0) 3.22-3.33 (2H, m), 3.42-3.61 (4H, m), 3.95 (3H, s), 4.38 (2H, d, J 7.0), 4.53 (2H, br d, J 14.5), 6.77 (1H, d, J 8.0), 7.10 (1H, t, J 8.0), 7.27 (1H, d, J 8.0), 7.61 (1H, s). EIMS; m/z=398.0 [M+H]$^+$.

15B: 1-{[1-(Cyclohexylmethyl)-7-methoxy-1H-indol-3-yl]carbonyl}-4-ethyl-2,3,5,6-tetramethylpiperazine, hydrochloride salt was prepared using 1-{[1-(cyclohexyl-methyl)-7-methoxy-1H-indol-3-yl]carbonyl}-2,3,5,6-tetramethylpiperazine. $^1$H NMR (400 MHz, CD$_3$OD) $\delta_H$ 0.98-1.29 (8H, m), 1.32 (3H, t, J 6.5), 1.44-1.88 (15H, m), 3.32-3.83 (5H, m), 3.95 (3H, s), 4.20-4.41 (3H, m), 6.77 (1H, d, J 8.0), 7.11 (1H, t, J 8.0), 7.27 (1H, d, J 8.5), 7.55 (1H, s). EIMS; m/z=440.2 [M+H]$^+$.

15C: 1-{[1-(Cyclohexylmethyl)-7-methoxy-1H-indol-3-yl]carbonyl}-2,6-dimethyl-4-ethylpiperazine, hydrochloride salt was prepared using 1-{[1-(cyclohexylmethyl)-7-methoxy-1H-indol-3-yl]carbonyl}-2,6-dimethylpiperazine. $^1$H NMR (400 MHz, CD$_3$OD) $\delta_H$ 0.97-1.22 (5H, m), 1.43 (3H, t, J 7.0), 1.49 (6H, d, J 8.0), 1.51-1.88 (6H, m), 3.23-3.41 (4H, m), 3.56 (2H, br d, J 11.0), 3.95 (3H, s), 4.26 (2H, d, J 7.0), 4.86 (2H, br s), 6.76 (1H, d, J 7.5), 7.1 (1H, t, J 8.0), 7.23 (1H, d, J 8.0), 7.48 (1H, s). EIMS; m/z=412.4 [M+H]$^+$.

15D: 1-{[1-(Cyclohexylmethyl)-7-methoxy-1H-indol-3-yl]carbonyl}-4-ethyl-3-methylpiperazine, hydrochloride salt was prepared using 1-{[1-(cyclohexylmethyl)-7-methoxy-1H-indol-3-yl]carbonyl}-3-methylpiperazine. $^1$H NMR (400 MHz, CD$_3$OD) $\delta_H$ 0.97-1.43 (11H, m), 1.56 (2H, br d, J 12.0), 1.64-1.89 (4H, m), 3.12-3.68 (7H, br m), 3.95 (3H, s), 4.26 (2H, d, J 7.0), 4.50 (2H, br s), 6.77 (1H, d, J 8.0), 7.10 (1H, t, J 8.0), 7.26 (1H, d, J 8.0), 7.54 (1H, s). EIMS; m/z=398.2 [M+H]$^+$.

15E: 1-{[1-(Cyclohexylmethyl)-7-methoxy-1H-indol-3-yl]carbonyl}-trans-2,5-dimethyl-4-ethylpiperazine, hydrochloride salt 1-{[1-(Cyclohexylmethyl)-7-methoxy-1H-indol-3-yl]carbonyl}-trans-2,5-dimethylpiperazine was prepared following the method in example 12, using 1-(cyclohexylmethyl)-7-methoxy-indole-3-carboxylic acid and trans-2,5-dimethylpiperazine. The procedure described under example 14 was used to afford the title compound. $^1$H NMR (400 MHz, CD$_3$OD) $\delta_H$ 0.97-1.32 (9H, m), 1.37 (3H, t, J 7.0), 1.44-1.89 (8H, m), 3.12-3.78 (6H, br m), 3.95 (3H, s), 4.17-4.33 (3H, m), 5.00 (1H, brs), 6.76 (1H, d, J 7.5), 7.10 (1H,t, J 8.0), 7.21 (1H, d, J 8.0), 7.48(1H, s). EIMS; m/z=412.4 [M+H]$^+$.

15F: 1-{[1-(cyclohexylmethyl)-7-methoxy-1H-indol-3-yl]carbonyl}-3,4,5-trimethylpiperazine, hydrochloride salt was prepared using 1-{[1-(cyclohexylmethyl)-7-methoxy-1H-indol-3-yl]carbonyl}-3,5-dimethylpiperazine and iodomethane. $^1$H NMR (400 MHz CD$_3$OD) $\delta_H$ 0.97-1.89 (17H, m), 2.96 (3H, brs), 3.23-3.48 (4H, brm), 3.05 (3H, s), 4.26 (2H, d, J 7.0), 4.49 (2H, br d, J 12.0), 6.77 (1H, d, J 7.5), 7.10 (1H, t, J 8.0), 7.26 (1H, d, J 7.5), 7.54 (1H, s). EIMS; m/z=398.0 [M+H]$^+$.

15G: 1-{[1-(cyclopentylmethyl)-7-methoxy-1H-indol-3-yl]carbonyl}-3,4,5-trimethylpiperazine, hydrochloride salt was prepared using 1-{[1-(cyclopentylmethyl)-7-methoxy-1H-indol-3-yl]carbonyl}-3,5-dimethylpiperazine and iodomethane. $^1$H NMR (400 MHz, CD$_3$OD) $\delta_H$ 1.23-1.70 (14H, m), 2.40 (1H, heptet, J 7.5), 2.96 (3H, brs), 3.21-3.48 (4H, br m), 3.95 (3H, s), 4.38 (2H, d, J 7.0), 4.50 (2H, br d, J 13.5), 6.77 (1H, d, J 7.5), 7.10 (1H, t, J 8.0), 7.26 (1H, d, J 8.0), 7.60 (1H, s). EIMS; m/z=384.2 [M+H]$^+$.

15H: 1-{[1-(cyclohexylmethyl)-7-methoxy-1H-indol-3-yl]carbonyl}-3,4-dimethylpiperazine, hydrochloride salt was prepared using 1-{[1-(cyclohexylmethyl)-7-methoxy-1H-indol-3-yl]carbonyl}-3-methylpiperazine and iodomethane. $^1$H NMR (400 MHz, CD$_3$OD) $\delta_H$ 0.97-1.89 (14H, m), 2.92 (3H, br s), 3.19-3.61 (5H, br m), 3.95 (3H, s), 4.26 (2H, d, J 7.0), 4.49 (2H, m), 6.76 (1H, d, J 7.5), 7.10 (1H, t, J 8.0), 7.27 (1H, d, J 8.0), 7.54 (1H, s). EIMS; m/z=384.2 [M+H]$^+$.

15I: (S)-1-{[1-(Cyclopentylmethyl)-7-methoxy-1H-indol-3-yl]carbonyl}-4-ethyl-3-methylpiperazine, hydrochloride salt was prepared using (S)-1-{[1-(cyclopentylmethyl)-7-methoxy-1H-indol-3-yl]carbonyl}-3-methylpiperazine and iodoethane. $^1$H NMR (400 MHz, CD$_3$OD) $\delta_H$ 1.24-1.42 (8H, m), 1.51-1.73 (6H, m), 2.43 (1H, heptet, J 7.6), 3.12-3.23 (2H, m), 3.47-3.71 (5H, br m), 3.95 (3H, s), 4.38 (2H, d, J 6.9), 4.51 (2H, brs), 6.77 (1H, d, J 8.2), 7.10 (1H, t, J 7.7), 7.26 (1H, d, J 8.1), 7.60 (1H, s). EIMS; m/z=384.2 [M+H]$^+$.

15J: (R)-1-{[1-(Cyclopentylmethyl)-7-methoxy-1H-indol-3-yl]carbonyl}-4-ethyl-3-methylpiperazine, hydrochloride salt was prepared using (R)-1-{[1-(cyclopentylmethyl)-7-methoxy-1H-indol-3-yl]carbonyl}-3-methylpiperazine (prepared as detailed in example 12) and iodoethane. $^1$H NMR (400 MHz, CD$_3$OD) $\delta_H$ 1.24-1.42 (8H, m), 1.51-1.73 (6H, m), 2.43 (1H, heptet, J 7.6), 3.12-3.23 (2H, m), 3.47-3.71 (5H, br m), 3.95 (3H, s), 4.38 (2H, d, J 6.9), 4.51 (2H, br s), 6.77 (1H, d, J 8.2), 7.10 (1H, t, J 7.7), 7.26 (1H, d, J 8.1), 7.60 (1H, s). EIMS; m/z=384.2 [M+H]$^+$.

15K: (S)-1-{[1-(Cyclopentylmethyl)-7-methoxy-1H-indol-3-yl]carbonyl}-3,4-dimethylpiperazine, hydrochloride salt was prepared using (S)-1-{[1-(cyclopentylmethyl)-7-methoxy-1H-indol-3-yl]carbonyl}-3-methylpiperazine and iodomethane. $^1$H NMR (400 MHz, CD$_3$OD) $\delta_H$ 1.27-1.42 (5H, m), 1.52-1.74 (6H, m), 2.43 (1H, heptet, J 7.4), 2.86-2.99 (3H, m), 3.17-3.60 (5H, br m), 3.95 (3H, s), 4.38 (2H, d, J 7.6), 4.52 (2H, brd, J 14.6), 6.77 (1H, d, J 7.9), 7.10 (1H, t, J 7.7), 7.27 (1H, d, J 8.1), 7.60 (1H, s). EIMS; m/z=370.0 [M+H]$^+$.

15L: (R)-1-{[1-(Cyclopentylmethyl)-7-methoxy-1H-indol-3-yl]carbonyl}-3,4-dimethylpiperazine, hydrochloride salt was prepared using (R)-1-{[1-(cyclopentylmethyl)-7-methoxy-1H-indol-3-yl]carbonyl}-3-methylpiperazine and iodomethane. $^1$H NMR (400 MHz, CD$_3$OD) $\delta_H$ 1.27-1.42 (5H, m), 1.52-1.74 (6H, m), 2.43 (1H, heptet, J 7.4), 2.86-2.99 (3H, m), 3.17-3.60 (5H, br m), 3.95 (3H, s), 4.38 (2H, d, J 7.6), 4.52 (2H, brd, J 14.6), 6.77 (1H, d, J 7.9), 7.10 (1H, t, J 7.7), 7.27 (1H, d, J 8.1), 7.60 (1H, s). EIMS; m/z=370.5 [M+H]$^+$.

15M: 1-{[1-(Cyclohexylmethyl)-7-methoxy-1H-indol-3-yl]carbonyl}-3,3-dimethyl-4-ethylpiperazine, hydrochloride salt was prepared using 1-{[1-(cyclohexylmethyl)-7-methoxy-1H-indol-3-yl]carbonyl}-3,3-dimethylpiperazine and iodoethane. $^1$H NMR (400 MHz, CD$_3$OD) $\delta_H$ 0.97-1.90 (20H, m), 2.82-3.69 (6H, br m), 3.95 (3H, s), 4.22-4.61 (4H, m), 6.77 (1H, d, J 7.9), 7.10 (1H, t, J 8.0), 7.25 (1H, d, J 8.1), 7.53 (1H, s). EIMS; m/z=412.4 [M+H]$^+$.

15N: 1-{[1-(Cyclohexylmethyl)-7-methoxy-1H-indol-3-yl]carbonyl}-3,3,4-trimethylpiperazine, hydrochloride salt was prepared using 1-{[1-(cyclohexylmethyl)-7-methoxy-1H-indol-3-yl]carbonyl}-3,3-dimethylpiperazine and iodomethane. $^1$H NMR (400 MHz, CD$_3$OD) $\delta_H$ 0.98-1.90 (17H, m), 2.85 (3H, s), 3.29-3.70 (4H, m), 3.95 (3H, s), 4.22-4.60 (4H, m), 6.77 (1H, d, J 7.7), 7.10 (1H, t, J 8.1), 7.25 (1H, d, J 8.2), 7.54 (1H, s). EIMS; m/z=398.2 [M+H]$^+$.

15O: (S)-1-{[1-(cyclohexylmethyl)-7-methoxy-1H-indol-3-yl]carbonyl}-3,4-dimethylpiperazine, hydrochloride salt was prepared using (S)-1-{[1-(cyclohexylmethyl)-7-methoxy-1H-indol-3-yl]carbonyl}-3-methylpiperazine and iodomethane. $^1$H NMR (400 MHz, CD$_3$OD) $\delta_H$ 0.97-1.89 (14H, m), 2.92 (3H, br s), 3.19-3.61 (5H, br m), 3.95 (3H, s), 4.26-(2H, d, J 7.0), 4.49 (2H, m), 6.76 (1H, d, J 7.5), 7.10 (1H, t, J 8.0), 7.27 (1H, d, J 8.0), 7.54 (1H, s). EIMS; m/z=384.2 [M+H]$^+$.

15P: (S)-1-{[1-(cyclohexylmethyl)-7-methoxy-1H-indol-3-yl]carbonyl}-3-methyl-4-(2-fluoroethyl)piperazine, hydrochloride salt was prepared using (S)-1-{[1-(cyclohexylmethyl)-7-methoxy-1H-indol-3-yl]carbonyl}-3-methylpiperazine and 1-bromo-2-fluoroethane. $^1$H NMR (400 MHz, CD$_3$OD) $\delta_H$ 0.96-1.90 (14H, m), 3.31-3.90 (7H, br m), 3.95 (3H, s), 4.26 (2H, d, J 7.0), 4.40-4.59 (2H, m), 4.68-5.04 (2H, br m), 6.77 (1H, d, J 7.5), 7.11 (1H, t, J 8.0), 7.27 (1H, d, J 8.0), 7.56 (1H, s). EIMS; m/z=416.0 [M+H]$^+$.

EXAMPLE 16

(R)-2-{[1-(Cyclohexylmethyl)-7-methoxy-1H-indol-3-yl]carbonyl}-octahydro-2H-pyrido[1,2-a]pyrazine To a solution of (R)-(+)-1-(tertbutoxycarbonyl)-2-piperidine carboxylic acid (2.00 g, 8.72 mmol) in dichloromethane (30 ml) were added glycine methyl ester hydrochloride (1.09 g, 8.72 mmol), 1-[3-(dimethylamino)propyl]-3-ethyl carbodiimide hydrochloride (2.01 g, 10.46 mmol), 1-hydroxybenzotriazole (1.22 g, 9.04 mmol) and triethylamine (2.43 ml, 17.4 mmol). The mixture was stirred under a stream of nitrogen for 18 hours. The resulting mixture was washed with 0.5M hydrochloric acid (20 ml), water (2×20 ml) and brine (20 ml), dried over sodium sulphate and concentrated to yield (R)-1-(tertbutoxycarbonyl)piperidine-2-carboxyglycine methyl ester as a colourless oil (2.47 g, 8.23 mmol).

(R)-1-(Tertbutoxycarbonyl)piperidine-2-carboxyglycine methyl ester (2.46 g, 8.20 mmol) was dissolved in trifluoroacetic acid (10 ml) and the resulting solution stirred for 1 hour. The trifluoroacetic acid was then removed to yield a colourless oil, which was dissolved in methanol (85 ml) and triethylamine (9.0 ml, 64.6 mmol) added. The resulting mixture was heated under reflux for 4 hours. The solution was then concentrated to afford a pale orange oil which was recrystallised from heptane 48%, ether 48%, 2-propanol 4%, to yield (R)-octahydro-1,4-dioxo-2H-pyrido[1,2-a]pyrazine as white crystals (0.66 g, 3.90 mmol).

(R)-Octahydro-1,4-dioxo-2H-pyrido[1,2-a]pyrazine (0.5 g, 2.98 mmol) was added portionwise to a stirred solution of lithium aluminium hydride (1M in tetrahydrofuran; 11.9 ml, 11.9 mmol). The resulting mixture was heated under reflux for 0.5 h. The solution was then cooled to 0° C. and treated dropwise with water (1.35 ml), 1 M sodium hydroxide solution (0.45 ml), then water (1.35 ml). Tetrahydrofuran (10 ml) was added and the solution stirred for 0.5 h, before filtration. The filter cake was washed with tetrahydrofuran (2×5 ml) and the combined filtrate and washings concentrated to yield (R)-octahydro-2H-pyrido[1,2-a]pyrazine as a yellow oil (0.29 g, 2.07 mmol).

To a solution of 1-(cyclohexylmethyl)-7-methoxy-1H-indole (0.49 g, 2.03 mmol) in 1,1,2,2-tetrachloroethane (2.5 ml), was added oxalyl chloride (0.19 ml, 2.13 mmol) with stirring under a stream of nitrogen. The mixture was heated at 120° C. for 2 hours. After cooling to room temperature, triethylamine (0.30 ml, 2.13 mmol) was added, followed by (R)-octahydro-2H-pyrido[1,2-a]pyrazine (0.28 g, 2.03 mmol) as a solution in 1,1,2,2-tetrachloroethane (2 ml). The solution was stirred at room temperature for 2 hours. Sodium hydroxide solution (1 M; 8 ml) was then added and the resulting mixture partitioned between dichloromethane (10 ml) and water (10 ml).

The organic layer was extracted, washed with water (10 ml), dried over sodium sulfate and concentrated. The resulting purple oil was purified by flash chromatography using 98% dichloromethane, 2% methanol as eluent to yield the title product as a pale brown oil (245 mg, 0.60 mmol). $[\alpha]_D^{22}$+13° (c 1.87 mg/ml in CHCl$_3$); $^1$H NMR (400 MHz, CDCl$_3$) $\delta_H$ 0.92-1.05 (2H, m), 1.12-1.36 (6H, m), 1.48-1.88 (9H, m), 1.93-1.98 (1H, m), 2.07 (1H, dt, J 11.5, 4.0), 2.24 (1H, dt, J 12.0, 3.0), 2.70-2.81 (3H, m), 2.84-2.86 (1H, m), 3.19-3.25 (2H, m), 3.93 (3H, s), 4.18 (2H, d, J 7.0), 4.18-4.32 (2H, m), 6.65 (1H, d, J 7.5), 7.07 (1H, dd, J 8.0, 7.5), 7.25 (1H, s), 7.29 (1H, d, J 8.0); EIMS: m/z=410.2 [M+H]$^+$.

EXAMPLE 17

The procedure described under Example 16 was further used to prepare the following compounds:

17A. (S)-2-{[1-(Cyclohexylmethyl)-7-methoxy-1H-indol-3-yl]carbonyl}-octahydro-2H-Pyrido[1,2-a]pyrazine, hydrochloride salt was prepared using (S)-(−)-1-(tertbutoxycarbonyl)-2-piperidine carboxylic acid. $[\alpha]_D^{22}$−18 (free base; c 4.05 mg/ml in CHCl$_3$); $^1$H NMR (400 MHz, CDCl$_3$) $\delta_H$ 0.99-1.08 (2H, m), 1.13-1.28 (3H, m), 1.50-2.03 (12H, m), 3.02-3.12 (1H, m), 3.13-3.30 (3H, m), 3.43-3.50 (3H, m), 3.95 (3H, s), 4.27 (2H, d, J 7.0), 4.49-4.59 (2H, m), 6.77 (1H, d, J 7.5), 7.11 (1H, dd, J 8.0, 7.5), 7.27 (1H, d, J 8.0), 7.54 (1H, s); EIMS: m/z=410.5 [M+H]$^+$.

17B. (R)-2-{[1-(Cyclohexylmethyl)-7-methoxy-1H-indol-3-yl]carbonyl}-octahydro-2H-pyrrolo[1,2-a]pyrazine was prepared using (R)-(+)-1-(tertbutoxycarbonyl)-2-pyrrolidine carboxylic acid. $^1$H NMR (400 MHz, CDCl$_3$) $\delta_H$ 0.92-1.04 (2H, m), 1.13-1.21 (3H, m), 1.40-1.45 (1H, m), 1.57-1.89 (9H, m), 2.00-2.10 (1H, m), 2.15-2.29 (2H, m), 2.76-2.85 (1H, m), 3.02-3.23 (3H, m), 3.93 (3H, s), 4.18 (2H, d, J 7.0), 4.32-4.56 (2H, m), 6.67 (1H, d, J 7.0), 7.08 (1H, t, J 8.0), 7.25-7.30 (2H, m); EIMS: m/z=396.2 [M+H]$^+$.

17C. (S)-2-{[1-(Cyclohexylmethyl)-7-methoxy-1H-indol-3-yl]carbonyl}-octahydro-2H-Pyrrolo[1,2-a]pyrazine, hydrochloride salt was prepared using (S)-(−)-1-(tertbutoxycarbonyl)-2-pyrrolidine carboxylic acid. $^1$H NMR of free base (400 MHz, CDCl$_3$) $\delta_H$ 0.93-1.03 (2H, m), 1.11-1.21 (3H, m), 1.35-1.46 (1H, m), 1.56-1.89 (9H, m), 1.96-2.05 (1H, m), 2.21-2.27 (2H, m), 2.77 (1H, t, J 11.0), 3.07 (1H, d, J 10.5), 3.08-3.20 (2H, m), 3.93 (3H, s), 4.18 (2H, d, J 7.0), 4.26-4.41 (1H, m), 4.43-4.56 (1H, m), 6.65 (1H, d, J 8.0), 7.07 (1H, t, J 8.0), 7.25-7.30 (2H, m).; EIMS: m/z=396.2 [M+H]$^+$.

17D: (S)-2-{[1-(Cyclopentylmethyl)-7-methoxy-1H-indol-3-yl]carbonyl}-octahydro-2H-pyrido[1,2-a]pyrazine, hydrochloride salt was prepared using (S)-(−)-1-(tertbutoxycarbonyl)-2-piperidine carboxylic acid and 1-(cyclopentylmethyl)-7-methoxy-1H-indole. $^1$H NMR (400 MHz, CD$_3$OD) $\delta_H$ 1.27-2.03 (14H, m), 2.41 (1H, heptet, J 7.0), 3.01-3.52 (7H, m), 3.95 (3H, s), 4.38 (2H, d, J 7.5), 4.52.(2H, dd, J 10.0, 7.0), 6.77 (1H, d, J 8.0), 7.1 (1H, t, J 8.0), 7.26 (1H, d, J 8.0), 7.6 (1H, s). EIMS; m/z=396.2 [M+H]$^+$.

17E: (S)-2-{[1-(Cyclopentylmethyl)-7-methoxy-1H-indol-3-yl]carbonyl}-octahydro-2H-pyrrolo[1,2-a]pyrazine, hydrochloride salt was prepared using (S)-(−)-1-(tertbutoxycarbonyl)-2-pyrrolidine carboxylic acid and 1-(cyclopentylmethyl)-7-methoxy-1H-indole. $^1$H NMR (400 MHz, CDCl$_3$) $\delta_H$ 1.21-2.23 (15H, m), 2.41 (1H, heptet, J 7.5), 2.75 (1H, t, J 11.0), 3.01-3.20 (3H, m), 3.94 (3H, s), 4.30 (2H, d, J 7.0), 4.32-4.53 (2H, m), 6.65 (1H, d, J 7.5), 7.07 (1H, t, J 7.5), 7.23-7.31 (2H, m). EIMS; m/z=382.2 [M+H]$^+$.

17F: (3R,9R)-2-{[1-(Cyclohexylmethyl)-7-methoxy-1H-indol-3-yl]carbonyl}-3-isobutyloctahydro-2H-pyrrolo[1,2-a]pyrazine, was prepared using (3R,9R)-octahydro-1,4-dioxo-2H-pyrrolo[1,2-a]pyrazine (commercially available) instead of (R)-octahydro-1,4-dioxo-2H-pyrido[1,2-a]pyrazine. EIMS; m/z=452.2 [M+H]$^+$.

17G: (3S,9 S)-2-{[1-(Cyclohexylmethyl)-7-methoxy-1H-indol-3-yl]carbonyl}-3-methyloctahydro-2H-pyrrolo[1,2-a]pyrazine was prepared using 1-(tertbutoxycarbonyl)proline and L-alanine methyl ester hydrochloride salt. EIMS; m/z=410.0 [M+H]$^+$.

17H: (2 R,αS)-1-{[1-(Cyclohexylmethyl)-7-methoxy-1H-indol-3-yl]carbonyl}-2-(α-hydroxy)ethyl-4-methylpiperazine was prepared using 1-methyl-1-(tertbutoxycarbonyl)glycine and D-threonine methyl ester hydrochloride salt. EIMS; m/z=414.2 [M+H]$^+$.

17I: (2 S,αR)-1-{[1-(Cyclohexylmethyl)-7-methoxy-1H-indol-3-yl]carbonyl}-2-(α-hydroxy)ethyl-4-methylpiperazine was prepared using 1-methyl-1-(tertbutoxycarbonyl)glycine and L-threonine methyl ester hydrochloride salt. EIMS; m/z=414.2 [M+H]$^+$.

17J: (S)-2-{[1-(Cyclohexylmethyl)-7-methoxy-1H-indol-3-yl]carbonyl}-3,3-dimethyloctahydro-2H-pyrrolo[1,2-a]pyrazine was prepared using 1-(tertbutoxycarbonyl)proline and aminoisobutyric acid methyl ester hydrochloride salt. EIMS; m/z=424.2 [M+H]$^+$.

EXAMPLE 18

1-{[1-(Cyclohexylmethyl)-7-methoxy-1H-indol-3-yl]carbonyl}-3-(fluoromethyl) piperazine, hydrochloride salt To a solution of 2,3-dibromopropionic acid ethyl ester (21.91 ml, 150.7 mmol) in toluene (175 ml) at 40° C. was added a mixture of N,N'-dibenzylethylenediamine (35.87 g, 149.2 mmol) and triethylamine (37 ml, 269 mmol) in toluene (75 ml). The mixture was heated to 80° C. for 16 h, filtered and the precipitate washed with toluene (200 ml). The combined filtrates were washed with water (2×200 ml), dried with magnesium sulfate and evaporated to afford 1,4-dibenzyl-piperazine-2-carboxylic acid ethyl ester (45.57 g) as an orange oil.

Lithium aluminium hydride (1 M solution in tetrahydrofuran, 32 ml, 32 mmol) at 0° C. was treated dropwise with a solution of 1,4-dibenzyl-piperazine-2-carboxylic acid ethyl ester (10 g, 32.1 mmol) in tetrahydrofuran (30 ml) and stirred for 16 hours. The mixture was quenched by slow addition of sodium hydroxide solution (4 M, 150 ml), followed by dichloromethane (200 ml). The organic phase was separated, dried with sodium sulfate and evaporated to afford 1,4-dibenzyl-2-(hydroxymethyl)piperazine (8.36 g) as an orange oil.

To a solution of diethylaminosulfur trifluoride (1.5 ml, 12.16 mmol) in dichloromethane (10 ml) at −72° C. was added 1,4-dibenzyl-2-(hydroxymethyl)piperazine (3 g, 10.1 mmol) in dichloromethane (20 ml) over 10 minutes. The mixture was stirred for 16 h whilst warming to room temperature and treated with water (20 ml). The aqueous phase was basified to pH 9 using 4 M sodium hydroxide and the organic phase separated. The aqueous phase was extracted with dichloromethane (2×30 ml) and the combined organic layers dried with sodium sulfate and evaporated. The residue was purified by flash chromatography eluting with 20% (v/v) ethyl acetate in hexane to afford 1,4-dibenzyl-2-(fluoromethyl)piperazine (0.94 g) as a colourless oil.

To a slurry of palladium on carbon (10% wt/wt, 1 g) in ethanol (20 ml) was added 1,4-dibenzyl-2-(fluoromethyl) piperazine (2.98 g, 10 mmol) in ethanol (20 ml). The mixture was heated to 65° C. under an hydrogen atmosphere (5 atm.) for 72 hours, filtered through dicalite and the dicalite washed with ethanol (50 ml). The filtrates were evaporated to afford 2-(fluoromethyl)piperazine (0.97 g) as a colourless solid.

To a solution of 1-(cyclohexyl)methyl-7-methoxy-indole-3-carboxylic acid (0.59 g, 2.04 mmol, prepared following the method in Example 1) and 2-(fluoromethyl) piperazine (0.37 g, 3.15 mmol) in dichloromethane (15 ml) was added 1-(3-dimethylaminopropyl)-3-ethylcarbodiimide hydrochloride (0.47 g, 2.45 mmol) and 1-hydroxy benzotriazole (0.07 g, 0.51 mmol). The mixture was stirred at room temperature for 18 h and evaporated. The residue was purified by flash chromatography eluting with 0-10% (v/v) methanol in dichloromethane to afford the title compound (free base) as a colourless oil (0.47 g). The free base (0.05 g) was dissolved in diethyl ether (3 ml) and treated dropwise with 2 M hydrochloric acid in diethyl ether (1 ml). The resulting precipitate was collected by filtration, washed with diethyl ether (10 ml) and dried under reduced pressure to afford the title compound (1:1 hydrochloric acid salt) as a colourless solid (0.05 g, 0.12 mmol). $^1$H NMR (400 MHz, CD$_3$OD) $\delta_H$ 0.98-1.27 (5H, m), 1.57 (2H, br d, J 12.9), 1.63-1.90 (4H, m), 3.21-3.53 (4H, m), 3.68-3.79 (1H, m) 3.95 (3H, s), 4.26 (2H, d, J 7.1), 4.43-4.82 (4H, m), 6.77 (1H, d, J 7.7), 7.11 (1H, t, J 7.5), 7.27 (1H, d, J 8.0), 7.57 (1H, s); EIMS: m/z 270.2 [Fragment+H]$^+$.

EXAMPLE 19

1-{[1-(Cyclohexylmethyl)-7-methoxy-1H-indol-3-yl]carbonyl}-3-(fluoromethyl)-4-cyclopropyl piperazine, hydrochloride salt To a solution of 1-{[1-(Cyclohexylmethyl)-7-methoxy-1H-indol-3-yl]carbonyl}-3-(fluoromethyl) piperazine (0.2 g, 0.52 mmol, prepared following the method in Example 18)

in methanol (10 ml) was added acetic acid (0.18 ml, 3.1 mmol), 4 Å molecular sieves (1 g), [(1-ethoxycyclopropyl)oxy] trimethylsilane (0.62 ml, 3.1 mmol) and sodium cyanoborohydride (0.15 g, 2.33 mmol). The mixture was heated to 70° C. for 18 h, filtered and the precipitate washed with dichloromethane (20 ml) and methanol (20 ml). The filtrates were evaporated, dissolved in dichloromethane (30 ml) and washed with sodium hydroxide solution (4 M, 15 ml) and saturated sodium chloride solution (15 ml). The organic phase was dried with sodium sulfate, evaporated and the residue purified by flash chromatography eluting with 2% (v/v) methanol in dichloromethane to afford the title compound (free base) as a yellow oil (0.2 g). The free base was dissolved in diethyl ether (3 ml) and treated dropwise with 2 M hydrochloric acid in diethyl ether (1 ml). The resulting precipitate was collected by filtration, washed with diethyl ether (10 ml) and dried under reduced pressure to afford the title compound (1:1 hydrochloric acid salt) as a colourless solid (0.2 g, 0.43 mmol). $^1$H NMR (400 MHz, CD$_3$OD) $\delta_H$ 0.91-1.25 (9H, m), 1.57 (2H, br d, J 12.6), 1.62-1.91 (4H, m), 2.8-2.93 (1H, m), 3.33-3.82 (5H, m), 3.96 (3H, s), 4.27 (2H, d, J 7.0), 4.43-4.86 (3H, m), 5.10-5.31 (1H, m), 6.77 (1H, d, J 7.3), 7.11 (1H, t, J 8.1), 7.28 (1H, d, J 8.1), 7.56 (1H, s); EIMS: m/z 428.2 [M+H]$^+$.

EXAMPLE 20

In-vitro Determination of Efficacy and Potency at the Human CB1 Receptor Expressed in CHO Cells Chinese Hamster Ovary (CHO) cells expressing the human CB1 receptor and a luciferase reporter gene were suspended in phenol red/serum free DMEM/F-12 nut mix containing penicillin/streptomycin (50U/50 µg/ml) and fungizone (1 µg/ml) and seeded into 96 well plates at a density of 3×10$^4$ cells per well (100 µl final volume). Cells were incubated overnight (approx. 18 h at 37° C., 5% CO$_2$/95% air) prior to assay.

The test compound (10 mM solution in DMSO) was diluted in F12 Nut Mix to give a range of stock solutions from 0.11 mM to 0.11 nM. The stock solutions (10 µl) were added directly to the relevant wells. The plates were incubated at 37° C. for 5 hours to allow agonist-induced expression of the luciferase enzyme. Under subdued light, LucLite substrate (Packard; reconstituted as per manufacturer's instructions; 100 µl) was added to each well. Plates were covered with Top Seal and then incubated at room temperature for 5 minutes before counting on the Packard TopCount (single photon counting, 0.01 minute count time, 5 minute count delay).

A "best-fit" curve was fitted by a minimum sum of squares method to the plot of counts per second (CPS) against compound concentration (M) to obtain an EC$_{50}$ value. Table 1 shows the pEC$_{50}$ values obtained for some representative compounds of the invention.

TABLE I

| Example | Chemical name | Chemical structure | pEC$_{50}$ |
| --- | --- | --- | --- |
| 2 | 1-{[1-(Cyclopentylmethyl)-7-methoxy-1H-indol-3-yl]carbonyl}-4-ethylpiperazine, hydrochloride salt | 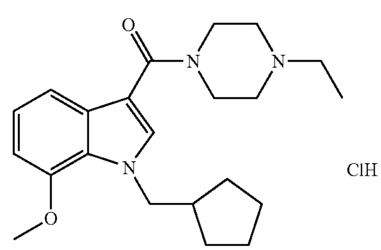 | 6.5 |
| 3C | 1-{[1-(Cyclohexylmethyl)-7-methoxy-1H-indol-3-yl]carbonyl}-4-(2-hydroxyethyl)piperazine, trifluoroacetic acid salt | 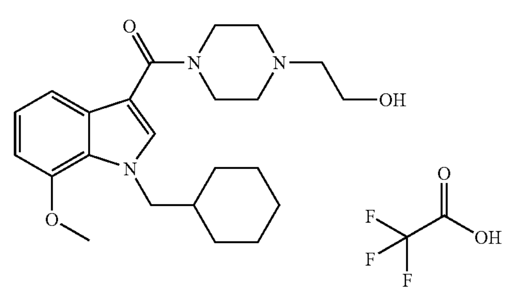 | 6.6 |
| 5B | 1-{[1-(Cyclohexylmethyl)-7-fluoro-1H-indol-3-yl)carbonyl}-4-ethylpiperazine, hydrochloride salt | 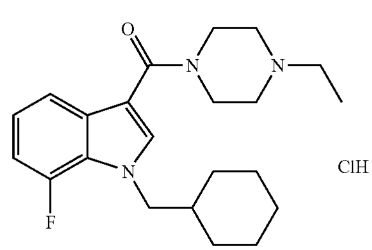 | 7.0 |

TABLE I-continued

| Example | Chemical name | Chemical structure | pEC$_{50}$ |
|---|---|---|---|
| (+)-51 | (+)-1-{[1-(1-Cyclohexylethyl)-1H-indol-3-yl]carbonyl)-4-ethylpiperazine, hydrochloride salt | 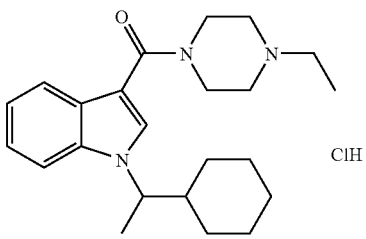 | 7.1 |
| 5Q | 1-{[1-(Cyclohex-3-enylmethyl)-7-methoxy-1H-indol-3-yl]carbonyl}-4-ethylpiperazine | 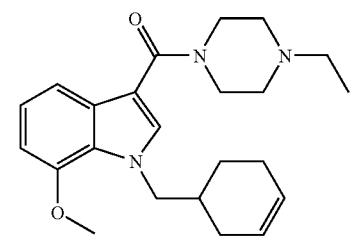 | 6.7 |
| 5T | 1-{[1-(Cyclohexylmethyl)-6-fluoro-1H-indol-3-yl]carbonyl}-4-methylpiperazine, hydrochloride salt | 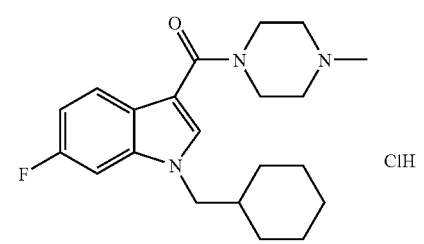 | 6.6 |
| 14 | 1-{[1-(Cyclohexylmethyl)-7-methoxy-1H-indol-3-yl]carbonyl}-3,5-dimethyl-4-ethylpiperazine, hydrochloride salt | 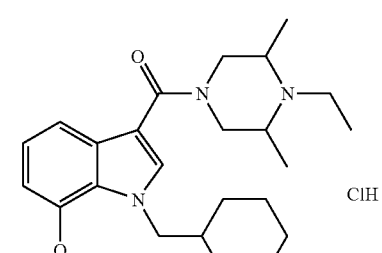 | 8.0 |
| 15F | 1-{[1-(cyclohexylmethyl)-7-methoxy-1H-indol-3-yl]carbonyl}-3,4,5-trimethylpiperazine, hydrochloride salt | 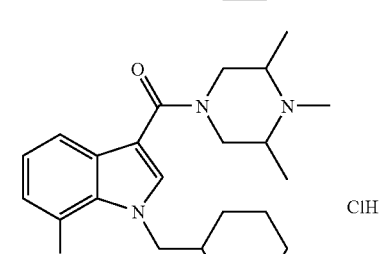 | 7.5 |
| 15O | (S)-1-{[1-(cyclohexylmethyl)-7-methoxy-1H-indol-3-yl]carbonyl}-3,4-dimethylpiperazine, hydrochloride salt | 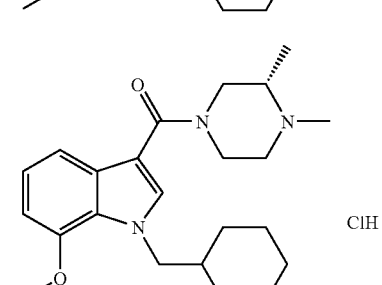 | 7.6 |

TABLE I-continued

| Example | Chemical name | Chemical structure | pEC$_{50}$ |
|---|---|---|---|
| 17A | (S)-2-{[1-(Cyclohexylmethyl)-7-methoxy-1H-indol-3-yl]carbonyl}-octahydro-2H-pyrido-[1,2-a]pyrazine, hydrochloride salt | 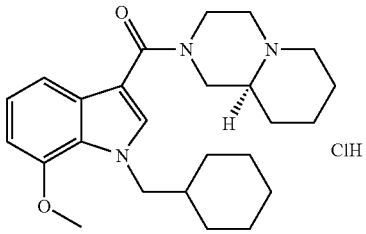 | 7.9 |
| 17C | (S)-2-{[1-(Cyclohexylmethyl)-7-methoxy-1H-indol-3-yl]carbonyl}-octahydro-2H-pyrrolo-[1,2-a]pyrazine, hydrochloride salt | 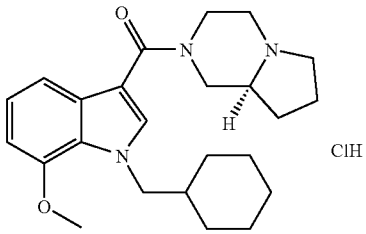 | 7.6 |
| 17D | (S)-2-{[1-(Cyclopentylmethyl)-7-methoxy-1H-indol-3-yl]carbonyl}-octahydro-2H-pyrido-[1,2-a]pyrazine, hydrochloride salt | 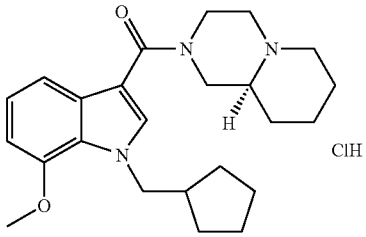 | 7.5 |
| Ref. 1 | 1-Ethyl-4-[[7-methoxy-1[2-(4-morpholin-yl)ethyl]1H-indazol-3-yl]carbonyl]-piperazine<br>Example 391 from WO0158869 | 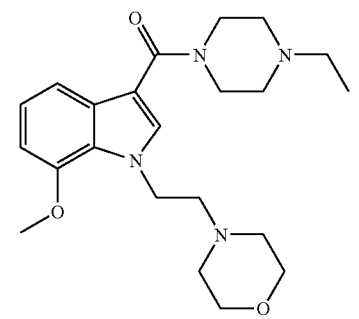 | <5 |
| Ref. 2 | 1-Ethyl-4-{[7-methoxy-1-[2-(4-morpholin-yl)ethyl]-1H-indol-3-y]carbonyl}-piperazine | 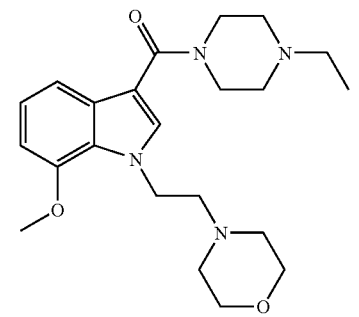 | <5 |

TABLE I-continued

| Example | Chemical name | Chemical structure | pEC$_{50}$ |
|---|---|---|---|
| Ref. 3. | 1-{[1-Benzyl-7-methoxy-1H-indol-3-yl]carbonyl}-4-ethylpiperazine | 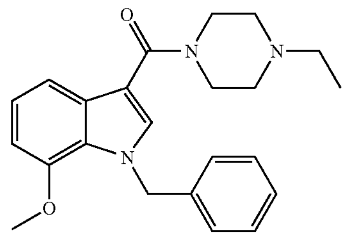 | <5 |

EXAMPLE 21

Tail Flick Latency in Mice

Mice were trained to sit still in a tail flick apparatus (Ugo Basile, Italy) whilst tail flick latency was measured. The tail was exposed to a focused beam of radiant heat at a point approximately 2.5 cm from the tip. Tail flick latency was defined as the interval between the appliance of the thermal stimulus and withdrawal of the tail. A 12 second cut-off was employed to prevent tissue damage. Four groups of eight mice were treated with vehicle or one of three doses of the test compound, administered intravenously (vehicle: saline 9 g/l; injection volume 10 ml/kg). Tail flick latency was measured before administration of the test compound and at regular intervals (typically 20, 40 and 60 minutes) after compound administration. The ED$_{50}$ was calculated at T$_{max}$.

The compounds of examples 14, 15F, 15O, 17A, 17C, and 17D significantly increased the tail flick latency with an ED$_{50}$<5 μmol/kg.

The invention claimed is:

1. An 1-[(indol-3-yl)carbonyl]piperazine derivative having the general formula I

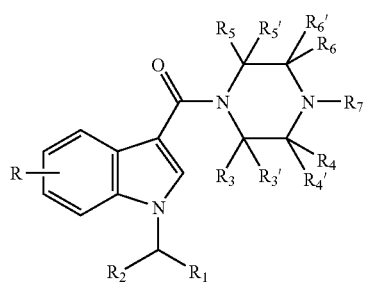

Formula I wherein
R represents 1-4 substituents independently selected from H, (C$_{1-4}$)alkyl (optionally substituted with halogen), (C$_{1-4}$)alkyloxy (optionally substituted with halogen), halogen, OH, NH$_2$, CN and NO$_2$;
R$_1$ is (C$_{5-8}$)cycloalkyl or (C$_{5-8}$)cycloalkenyl;
R$_2$ is H, methyl or ethyl;
R$_3$, R$_3$', R$_4$' R$_4$', R$_5$, R$_5$' and R$_6$' are independently hydrogen or (C$_{1-4}$)alkyl, optionally substituted with (C$_{1-4}$)alkyloxy, halogen or OH;
R$_6$ is hydrogen or (C$_{1-4}$)alkyl, optionally substituted with (C$_{1-4}$)alkyloxy, halogen or OH; or
R$_6$ forms together with R$_7$ a 4-7 membered saturated heterocyclic ring having only carbons as additional ring members; or
R$_7$ is H, (C$_{1-4}$)alkyl or (C$_{3-5}$)cycloalkyl, the alkyl groups being optionally substituted with OH, halogen or (C$_{1-4}$)alkyloxy; or
a pharmaceutically acceptable salt thereof.

2. The 1-[(indol-3-yl)carbonyl]piperazine derivative of claim 1, wherein R$_2$ is H and R$_1$ is (C$_{5-8}$)cycloalkyl.

3. The 1-[(indol-3-yl)carbonyl]piperazine derivative of claim 2, wherein R is (C$_{1-4}$)alkyloxy or halogen.

4. The 1-[(indol-3-yl)carbonyl]piperazine derivative of claim 3, wherein R represents a methoxy group at the 7-position of the indole ring.

5. The 1-[(indol-3-yl)carbonyl]piperazine derivative of claim 4, wherein R$_3$, R$_3$', R$_4$', R$_5$, R$_5$' and R$_6$' are H; R$_4$, R$_6$ and R$_7$ are independently H or (C$_{1-4}$)alkyl; or R$_6$ forms together with R$_7$ a 5- or 6-membered saturated heterocyclic ring and R$_4$ is H or (C$_{1-4}$)alkyl.

6. The 1-[(indol-3-yl)carbonyl]piperazine derivative according to claim 1, wherein the derivative is selected from the group consisting of
1-{[1-(cyclohexylmethyl)-7-methoxy-1H-indol-3-yl]carbonyl}-3,5-dimethyl-4-ethylpiperazine;
1-{[1-(cyclohexylmethyl)-7-methoxy-1H-indol-3-yl]carbonyl}-3,4,5-trimethylpiperazine;
(S)-1-{[1-(cyclohexylmethyl)-7-methoxy-1H-indol-3-yl]carbonyl}-3,4-dimethylpiperazine;
(S)-2-{[1-(cyclohexylmethyl)-7-methoxy-1H-indol-3-yl]carbonyl}-octahydro-2H-pyrido-[1,2-a]pyrazine;
(S)-2-{[1-(cyclohexylmethyl)-7-methoxy-1H-indol-3-yl]carbonyl}-octahydro-2H-pyrrolo-[1,2-a]pyrazine; and
(S)-2-{[1-(cyclopentylmethyl)-7-methoxy-1H-indol-3-yl]carbonyl}-octahydro-2H-pyrido-[1,2-a]pyrazine;
or a pharmaceutically acceptable salt thereof of each individual derivative.

7. A pharmaceutical composition, comprising:
the 1-[(indol-3-yl)carbonyl]piperazine derivative of claim 1, and
a pharmaceutically acceptable carrier.

8. A method of treating pain in a patient in need thereof, comprising:
administering an effective amount of the derivative according to claim 1.

* * * * *

UNITED STATES PATENT AND TRADEMARK OFFICE
CERTIFICATE OF CORRECTION

PATENT NO. : 7,304,064 B2
APPLICATION NO. : 10/518279
DATED : December 4, 2007
INVENTOR(S) : Philip Martin Cowley et al.

Page 1 of 1

It is certified that error appears in the above-identified patent and that said Letters Patent is hereby corrected as shown below:

Col. 29 Claim 1, lines 61-63 :

R3, R3', R4' R4', R5, R5' and R6' are independently hydrogen or (C1-4)alkyl, optionally substituted with (C1-4)alkyloxy, halogen or OH;

should read

R3, R3', R4, R4', R5, R5' and R6' are independently hydrogen or (C1-4)alkyl, optionally substituted with (C1-4)alkyloxy, halogen or OH;

Signed and Sealed this

First Day of April, 2008

JON W. DUDAS
*Director of the United States Patent and Trademark Office*